(12) United States Patent
Lee et al.

(10) Patent No.: US 6,710,165 B2
(45) Date of Patent: Mar. 23, 2004

(54) IGE-DEPENDENT HISTAMINE-RELEASING FACTOR-BINDING PEPTIDES

(75) Inventors: Kyunglim Lee, College of Pharmacy, Ewha Womans University, 11-1, Daehyun-dong, Seodaemun-ku, Seoul, 120-750 (KR); Junho Chung, Seoul (KR); Wha Jung Kim, Seoul (KR); Miyoung Kim, Seoul (KR); Jaehoon Jung, Seoul (KR)

(73) Assignee: Kyunglim Lee, Seoul (KR)

( * ) Notice: Subject to any disclaimer, the term of this patent is extended or adjusted under 35 U.S.C. 154(b) by 64 days.

(21) Appl. No.: 09/870,472

(22) Filed: Jun. 1, 2001

(65) Prior Publication Data

US 2002/0095023 A1 Jul. 18, 2002

(30) Foreign Application Priority Data

Jun. 1, 2000 (KR) ......................... 2000-30130

(51) Int. Cl.$^7$ .................. A61K 38/00; C07K 14/00
(52) U.S. Cl. ................ 530/300; 424/84; 514/2
(58) Field of Search .................. 530/300; 424/84; 514/2

(56) References Cited

PUBLICATIONS

MacDonald et al., *Springer Semin Immunopathol*, 1990, 12: 415–428.
MacDonald, *Current Opinion in Immunology*, 1996, 8:778–783.
Grant et al., *J. Allergy and Clinical Immunology*, 1991, 88(5): 683–693.
Charlesworth et al., *Int. Arch. Allergy Appl. Immunol.*, 1989, 88:50–53.
Alam et al., *J. Allergy Clin. Immunol.*, 1987, 79:103–108.
Pasmans et al., *Am. J. Respir. Crit Care Med.*, 1996, 154: 318–323.
Paradis et al., *Clin. and Experimental Allergy*, 1996, 26: 815–820.
Boireau et al., *Neuroreport.*, 1994, 5(18): 2657–2660 (Abstract Only).
Boireau et al., *Neuroreport.*, 1994, 5(16): 2157–2160 (Abstract Only).
Obinu et al., *Mov. Disord.*, 2002, 17(1): 13–19 (Abstract Only).
Boireau et al., *J Pharm. Pharmacol.*, 1998, 50(11): 1293–1297 (Abstract Only).
Keita et al., *Anesthesiology*, 1997, 87(5): 1164–1171 (Abstract Only).
Jehle et al., *Br. J. Pharmacol.*, 2000, 130(6): 1227–1234 (Abstract Only).
J. Bhisutthibhan et al., The Journal of Biological Chemistry, vol. 273, No. 26, Jun. 26, pp. 16192–16198, (1998).
J. Schroeder et al., The Journal of Immunology, 1997, vol. 159(1), pp. 447–452.
S. MacDonald et al., Science, vol. 269, (Aug. 4, 1995), pp. 688–690.
C. Sanchez et al., Electrophoresis, (1997), vol. 18, pp. 638–641.
Y. Gachet et al., The Journal of Cell Science, vol. 112, pp. 1257–1271, (1999).
C. Bachert, Clinical and Experimental Allergy, vol. 28, Supplement 6, pp. 15–19, 1998.

*Primary Examiner*—Gary Kunz
*Assistant Examiner*—Fozia Hamud
(74) *Attorney, Agent, or Firm*—JHK Law

(57) ABSTRACT

Disclosed are IgE-dependent histamine-releasing factor (HRF) receptor, HRF-binding peptides and nucleic acids encoding the same, and uses thereof in the medicinal area.

10 Claims, 37 Drawing Sheets

```
              1                                                       50
       a1  VANVPEVLLA TVTVCLTLTA KRMARKNCLV KNLEAVETLG STSTICSDKT
       a2  VANVPEGLLA TVTVCLTLTA KRMARKNCLV KNLEAVETLG STSTICSDKT
       a3  VANVPEGLLA TVTVCLTLTA KRMARKNCLV KNLEAVETLG STSTICSDKT
Consensus  VANVPEgLLA TVTVCLTLTA KRMARKNCLV KNLEAVETLG STSTICSDKT 51                                                      100
       a1  GTLTQNRMTV AHMWFDNQIH EADTTENQSG VSFDKTSATW FALSRIAGLC
       a2  GTLTQNRMTV AHMWFDNQIH EADTTEDQSG ATFDKRSPTW TALSRIAGLC
       a3  GTLTQNRMTV AHMWFDNQIH EADTTEDQSG TSFDKSSHTW VALSHIAGLC
Consensus  GTLTQNRMTV AHMWFDNQIH EADTTE#QSG .sFDK.S.TW .ALSrIAGLC 101                                                      150
       a1  NRAVFQANQE NLPILKRAVA GDASESALLK CIEVCCGSVM EMREKYTKIV
       a2  NRAVFKAGQE NISVSKRDTA GDASESALLK CIELSCGSVR KMRDRNPKVA
       a3  NRAVFKGGQD NIPVLKRDVA GDASESALLK CIELSSGSVK LMRERNKKVA
Consensus  NRAVFkagQ# Nip!lKRdvA GDASESALLK CIElscGSV. .MR#rn.K!a 151                                                      200
       a1  EIPFNSTNKY QLSIHKNPNA SEPKHLLVMK GAPERILDRC SSILLHGKEQ
       a2  EIPFNSTNKY QLSIHERED. SPQSHVLVMK GAPERILDRC STILVQGKEI
       a3  EIPFNSTNKY QLSIHETEDP NDNRYLLVMK GAPERILDRC ATILLQGKEQ
Consensus  EIPFNSTNKY QLSIHe.e#. s...hlLVMK GAPERILDRC stILlqGKEq 201                                                      250
       a1  PLDEELKDAF QNAYLELGGL GERVLGFCHL LLPDEQFPEG FQFDTDEVNF
       a2  PLDKEMQDAF QNAYMELGGL GERVLGFCQL NLPSGKFPRG FKFDTDELNF
       a3  PLDEEMKEAF QNAYLELGGL GERVLGFCHY YLPEEQFPKG FAFDCDDVNF
Consensus  PLDeE$k#AF QNAY$ELGGL GERVLGFChl .LP.eqFP.G F.FDtD#vNF 251                                                      300
       a1  PVDNLCFVGL ISMIDPPRAA VPDAVGKCRS AGIKVIMVTG DHPITAKAIA
       a2  PTEKLCFVGL MSMIDPPRAA VPDAVGKCRS AGIKVIMVTG DHPITAKAIA
       a3  TTDNLCFVGL MSMIDPPRAA VPDAVGKCRS AGIKVIMVTG DHPITAKAIA
Consensus  pt#nLCFVGL mSMIDPPRAA VPDAVGKCRS AGIKVIMVTG DHPITAKAIA 301                                                      350
       a1  KGVGIISEGN ETVEDIAARL NIPVNQVNPR DAKACVVHGS DLKDMTSEEL
       a2  KGVGIISEGN ETVEDIAARL NIPVSQVNPR EAKACVVHGS DLKDMTSEQL
       a3  KGVGIISEGN ETVEDIAARL NIPVSQVNPR DAKACVIHGT DLKDFTSEQI
Consensus  KGVGIISEGN ETVEDIAARL NIPVsQVNPR #AKACV!HGs DLKDmTSE#l
```

FIG. 18a

```
              351                                                      400
          a1  DDILRYHTEI VFARTSPQQK LIIVEGCQRQ GAIVAVTGDG VNDSPALKKA
          a2  DEILRDHTEI VFARTSPQQK LIIVEGCQRQ GAIVAVTGDG VNDSPALKKA
          a3  DEILQNHTEI VFARTSPQQK LIIVEGCQRQ GAIVAVTGDG VNDSPALKKA
   Consensus  D#ILr.HTEI VFARTSPQQK LIIVEGCQRQ GAIVAVTGDG VNDSPALKKA 401                                                  446
          a1  DIGVAMGIVG SDVSKQAADM ILLDDNFASI VTGVEEGRLI FDNLKK
          a2  DIGIAMGISG SDVSKQAADM ILLDDNFASI VTGVEEGRLI FDNLKK
          a3  DIGVAMGIAG SDVSKQAADM ILLDDNFASI VTGVEEGRLI FDNLKK
   Consensus  DIG!AMGI.G SDVSKQAADM ILLDDNFASI VTGVEEGRLI FDNLKK
```

Consensus symbols:
 ! is anyone of IV
 $ is anyone of LM
 % is anyone of FY
 # is anyone of NDQEBZ

FIG. 18b

```
              1                                                    50
         a1   GTAGCCAACG TGCCGGAAGT TTTGCTGGCC ACCGTCACGG TATGTCTGAC
         a2   GTAGCCAACG TCCCCGAAGG GCTCTTGGCC ACTGTTACTG TGTGCCTGAC
         a3   GTGGCCAATG TCCCAGAGGG GCTGCTGGCT ACTGTCACGG TGTGTCTGAC
Consensus     GTaGCCAAcG TcCC.GAaGg gcTgcTGGCc ACtGTcACgG TgTGtCTGAC 51                                                   100
         a1   GCTCACTGCC AAGCGCATGG CCAGGAAGAA CTGCCTGGTG AAGAACCTGG
         a2   GCTGACAGCC AAGCGCATGG CTCGCAAGAA CTGCCTGGTG AAGAACCTGG
         a3   GCTGACCGCC AAGCGCATGG CTCGGAAGAA CTGTCTGGTA AAGAACCTGG
Consensus     GCTgAC.GCC AAGCGCATGG CtcGgAAGAA CTGcCTGGTg AAGAACCTGG 101                                                  150
         a1   AAGCTGTGGA GACCTTGGGG TCCACATCCA CCATCTGCTC CGACAAGACT
         a2   AGGCGGTGGA GACGCTGGGC TCCACGTCCA CCATCTGCTC GGACAAGACA
         a3   AGGCGGTGGA GACGCTAGGC TCCACATCCA CCATCTGCTC CGACAAGACC
Consensus     AgGCgGTGGA GACgcTgGGc TCCACaTCCA CCATCTGCTC cGACAAGAC.

151                                                  200
         a1   GGAACTCTGA CTCAGAACCG GATGACAGTG GCTCACATGT GGTTTGACAA
         a2   GGCACCCTCA CCCAGAACCG CATGACGGTG GCTCACATGT GGTTTGACAA
         a3   GGCACCCTCA CCCAGAACCG CATGACCGTC GCCCACATGT GGTTTGACAA
Consensus     GGcACcCTcA CcCAGAACCG cATGAC.GTg GCtCACATGT GGTTTGACAA 201                                                  250
         a1   TCAAATCCAT GAAGCTGACA CCACAGAGAA TCAGAGTGGG GTCTCCTTTG
         a2   CCAGATCCAT GAGGCTGACA CCACTGAAGA TCAGTCTGGG GCCACTTTTG
         a3   CCAGATCCAC GAGGCCGACA CTACTGAGGA TCAGTCAGGG ACCTCTTTCG
Consensus     cCAgATCCAt GAgGCtGACA CcACtGAggA TCAGtctGGG gcCtCtTTtG 251                                                  300
         a1   ACAAGACGTC AGCCACCTGG TTCGCTCTGT CCAGAATTGC TGGTCTCTGT
         a2   ACAAGCGGTC CCCGACGTGG ACAGCCCTGT CTCGGATCGC TGGTCTCTGC
         a3   ACAAGAGCTC ACACACCTGG GTGGCCCTGT CCCACATCGC CGGTCTCTGC
Consensus     ACAAGagGTC acccACcTGG .t.GCcCTGT Cccg.ATcGC tGGTCTCTGc 301                                                  350
         a1   AACAGGGCAG TGTTTCAGGC TAACCAGGAA AACCTGCCTA TCCTGAAGCG
         a2   AATCGTGCCG TCTTCAAGGC TGGGCAGGAG AACATCTCCG TGTCTAAGCG
         a3   AACCGGGCTG TCTTCAAGGG CGGGCAGGAT AACATCCCTG TACTCAAGAG
Consensus     AAccGgGC.G TcTTcaAGGc tgggCAGGA. AACaTccCtg T.ct.AAGcG
```

FIG. 19a

```
            351                                              400
      a1    TGCAGTAGCG GGAGATGCTT CCGAGTCGGC GCTCCTAAAG TGCATCGAGG
      a2    GGACACAGCT GGTGACGCCT CTGAGTCAGC TCTGCTCAAG TGCATCGAGT
      a3    GGACGTGGCG GGTGATGCCT CAGAGTCCGC CCTGCTTAAG TGCATCGAGC
Consensus   gGacgtaGCg GGtGAtGCcT C.GAGTC.GC .CTgCT.AAG TGCATCGAG.

401                                              450
      a1    TCTGCTGTGG CTCCGTGATG GAGATGAGGG AGAAGTACAC CAAGATAGTG
      a2    TGTCCTGTGG CTCAGTGAGG AAGATGAGGG ACAGGAATCC CAAGGTGGCA
      a3    TGTCCTCGGG TTCCGTAAAG CTGATGCGCG AACGAAACAA GAAAGTGGCC
Consensus   TgTcCTgtGG cTCcGTgA.G .aGATGaGgG A.aggaAcac cAAggTgGc.

451                                              500
      a1    GAGATTCCTT TCAACTCCAC CAACAAGTAC CAGCTCTCCA TTCACAAGAA
      a2    GAAATTCCCT TCAACTCTAC CAACAAATAT CAGCTTTCCA TCCATGAGAG
      a3    GAGATTCCCT TCAACTCCAC TAACAAATAC CAGCTATCCA TCCATGAGAC
Consensus   GAgATTCCcT TCAACTCcAC cAACAAaTAc CAGCT.TCCA TcCAtgAGA.

501                                              550
      a1    CCCAAACGCA TCGGAGCCTA AGCACCTGCT AGTGATGAAG GGCGCCCCAG
      a2    GGAAGACAGC CCCCAGAGCC ATGTGCTG.. .GTGATGAAA GGTGCCCCGG
      a3    TGAGGACCCC AATGACAACC GATACCTGTT AGTGATGAAG GGCGCCCCTG
Consensus   .gaagAC.cc .c.gAga.cc a...acCTG.t aGTGATGAAg GGcGCCCC.G 551                                              600
      a1    AAAGGATCCT GGACCGATGC AGTTCTATCC TCCTCCACGG CAAGGAGCAG
      a2    AGCGCATCCT GGACCGATGC TCTACCATCC TGGTACAGGG CAAGGAGATC
      a3    AACGCATTCT GGACCGCTGT GCGACCATCC TCCTGCAGGG CAAGGAGCAG
Consensus   AacGcATcCT GGACCGaTGc .ctaCcATCC TccT.CAgGG CAAGGAGcag 601                                              650
      a1    CCCCTGGACG AAGAGCTGAA GGACGCCTTT CAGAATGCCT ACCTGGAGCT
      a2    CCTCTTGACA AGGAGATGCA AGATGCCTTT CAAAACGCCT ACATGGAGCT
      a3    CCTCTGGATG AGGAGATGAA GGAGGCCTTC CAGAACGCCT ACCTGGAGCT
Consensus   CCtCTgGAcg AgGAGaTGaA gGA.GCCTTt CAgAAcGCCT ACcTGGAGCT 651                                              700
      a1    GGGTGGCCTG GGAGAACGTG TGCTAGGTTT CTGCCACCTC CTTCTGCCTG
      a2    GGGAGGACTC GGGGAGCGAG TGCTGGGCTT CTGTCAGCTG AACCTGCCTT
      a3    TGGTGGCCTG GGCGAGCGTG TGCTGGGTTT CTGCCATTAC TACCTGCCGG
Consensus   gGGtGGcCTg GG.GAgCGtG TGCTgGGtTT CTGcCA.ctc .acCTGCCtg 701                                              750
      a1    ACGAACAGTT TCCTGAAGGC TTCCAGTTTG ACACTGATGA AGTCAATTTC
      a2    CTGGAAAGTT TCCTCGGGGC TTCAAATTTG ACACGGATGA GCTGAACTTT
```

FIG. 19b

```
        a3  AGGAACAGTT CCCCAAGGGC TTTGCCTTTG ACTGTGATGA CGTGAACTTC
Consensus   a.GaAcAGTT tCCt.agGGC TTc.a.TTTG ACactGATGA .gTgAAcTTc 751                                                800
        a1  CCCGTGGATA ACCTCTGCTT CGTGGGTCTT ATCTCCATGA TTGACCCTCC
        a2  CCCACAGAGA AGCTCTGCTT TGTGGGGCTC ATGTCTATGA TTGATCCCCC
        a3  ACCACAGACA ACCTTTGCTT CGTGGGTCTC ATGTCCATGA TCGACCCTCC
Consensus   cCCacaGA.A AcCTcTGCTT cGTGGGtCTc ATgTCcATGA TtGAcCCtCC 801                                                850
        a1  TCGAGCTGCT GTCCCCGATG CTGTGGGCAA ATGCCGCAGC GCTGGGATTA
        a2  CAGAGCAGCT GTGCCAGATG CTGTGGGCAA GTGCAGAAGT GCAGGCATCA
        a3  CCGGGCAGCT GTCCCTGATG CTGTGGGCAA ATGCCGCAGT GCAGGCATCA
Consensus   ccGaGCaGCT GTcCC.GATG CTGTGGGCAA aTGCcGcAGt GCaGGcATcA 851                                                900
        a1  AGGTCATCAT GGTCACAGGA GACCATCCAA TCACAGCCAA AGCCATTGCT
        a2  AGGTGATCAT GGTGACTGGG GATCACCCTA TCACAGCCAA GGCCATTGCC
        a3  AGGTCATCAT GGTCACCGGC GATCACCCCA TCACTGCGAA GGCCATCGCC
Consensus   AGGTcATCAT GGTcAC.GG. GAtCAcCC.A TCACaGCcAA gGCCATtGCc 901                                                950
        a1  AAGGGGGTGG GCATTATCTC AGAAGGTAAC GAGACCGTGG AAGACATTGC
        a2  AAAGGTGTGG GCATCATATC AGAGGGTAAC GAGACTGTGG AAGACATTGC
        a3  AAAGGTGTAG GCATCATCTC CGAGGGTAAC GAGACTGTGG AGGACATCGC
Consensus   AAaGGtGTgG GCATcATcTC aGAgGGTAAC GAGACtGTGG AaGACATtGC 951                                               1000
        a1  TGCCCGCCTC AACATTCCAG TGAACCAGGT GAACCCCAGA GATGCCAAGG
        a2  AGCCAGGCTC AACATTCCTG TGAGTCAAGT CAATCCCAGA GAAGCCAAGG
        a3  TGCCCGGCTC AACATCCCTG TCAGCCAGGT CAACCCCAGG GATGCCAAAG
Consensus   tGCCcGgCTC AACATtCCtG TgAgcCAgGT cAAcCCCAGa GAtGCCAAgG 1001                                              1050
        a1  CCTGTGTAGT ACATGGCAGT GACTTGAAGG ACATGACCTC TGAGGAGCTG
        a2  CATGTGTAGT GCACGGCTCA GACCTGAAGG ACATGACTTC AGAGCAGCTG
        a3  CCTGTGTGAT TCATGGCACC GACCTCAAGG ACTTCACCTC TGAGCAGATT
Consensus   CcTGTGTagT .CAtGGCac. GACcTgAAGG ACaTgACcTC tGAGcAGcTg
```

FIG. 19c

```
         1051                                                   1100
      a1 GATGACATTT TGCGGTACCA CACGGAGATT GTCTTTGCTA GGACCTCTCC
      a2 GATGAGATCC TCAGGGACCA CACGGAGATC GTGTTTGCCC GGACCTCCCC
      a3 GACGAGATCC TACAGAACCA CACTGAGATC GTCTTTGCCC GAACCTCCCC
Consensus GAtGAgATcc T.cgG.ACCA CACgGAGATc GTcTTTGCcc GgACCTCcCC 1101                                                   1150
      a1 TCAACAGAAG CTCATCATTG TGGAGGGCTG CCAGCGGCAG GGTGCCATCG
      a2 TCAGCAGAAG CTCATCATTG TGGAGGGCTG TCAGAGGCAG GGAGCCATCG
      a3 TCAGCAGAAG CTCATCATCG TGGAGGGCTG TCAGAGACAG GGAGCAATTG
Consensus TCAgCAGAAG CTCATCATtG TGGAGGGCTG tCAGaGgCAG GGaGCcATcG 1151                                                   1200
      a1 TGGCTGTCAC AGGGGATGGT GTCAATGACT CTCCAGCTTT GAAAAAGGCA
      a2 TGGCAGTGAC TGGTGACGGG GTGAACGACT CCCCCGCGCT GAAGAAGGCT
      a3 TGGCTGTGAC TGGCGATGGT GTGAATGACT CCCCTGCTCT GAAGAAGGCT
Consensus TGGCtGTgAC tGG.GAtGGt GTgAAtGACT CcCC.GCtcT GAAgAAGGCt 1201                                                   1250
      a1 GATATTGGGG TTGCCATGGG GATTGTTGGC TCGGATGTGT CCAAGCAAGC
      a2 GACATTGGCA TTGCCATGGG CATCTCTGGC TCTGATGTCT CTAAGCAGGC
      a3 GATATTGGGG TGGCCATGGG CATTGCTGGC TCTGATGTCT CTAAGCAGGC
Consensus GAtATTGGgg TtGCCATGGG cATtgcTGGC TCtGATGTcT CtAAGCAgGC 1251                                                   1300
      a1 TGCTGACATG ATTCTTCTGG ATGACAACTT TGCCTCCATC GTGACTGGAG
      a2 AGCTGACATG ATCCTTCTCG ACGACAACTT TGCCTCCATT GTGACGGGCG
      a3 TGCCGACATG ATTCTGCTGG ATGACAATTT TGCTTCCATT GTCACTGGTG
Consensus tGCtGACATG ATtCTtCTgG AtGACAAcTT TGCcTCCATt GTgACtGG.G 1301             1338
      a1 TAGAAGAAGG TCGTCTGATA TTTGATAACT TGAAGAAA
      a2 TGGAGGAGGG GCGCCTGATC TTTGACAACC TGAAGAAG
      a3 TGGAGGAAGG CCGCCTGATC TTTGACAACC TGAAGAAA
Consensus TgGAgGAaGG .CGcCTGATc TTTGAcAACc TGAAGAAa
```

Consensus symbols:
! is anyone of IV
$ is anyone of LM
% is anyone of FY
# is anyone of NDQEBZ

FIG. 19d

```
              1                                                           50
humana1   VANVPEGLLA TVTVCLTLTA KRMARKNCLV KNLEAVETLG STSTICSDKT
humana3   VANVPEGLLA TVTVCLTVTA KRMARKNCLV KNLEAVETLG STSTICSDKT
humana2   VANVPEGLLA TVTVCLTLTA KRMARKNCLV KNLEAVETLG STSTICSDKT
Consensus VANVPEGLLA TVTVCLT1TA KRMARKNCLV KNLEAVETLG STSTICSDKT 51                                                          100
humana1   GTLTQNRMTV AHMWFDNQIH EADTTENQSG VSFDKTSATW LALSRIAGLC
humana3   GTLTQNRMTV AHMWFDNQIH EADTTEDQSG TSFDKSSHTW VALSHIAGLC
humana2   GTLTQNRMTV AHMWFDNQIH EADTTEDQSG ATFDKRSPTW TALSRIAGLC
Consensus GTLTQNRMTV AHMWFDNQIH EADTTE#QSG .sFDK.S.TW .ALSrIAGLC 101                                                         150
humana1   NRAVFQANQE NLPILKRAVA GDASESALLK CIELCCGSVK EMRERYAKIV
humana3   NRAVFKGGQD NIPVLKRDVA GDASESALLK CIELSSGSVK LMRERNKKVA
humana2   NRAVFKAGQE NISVSKRDTA GDASESALLK CIELSCGSVR KMRDRNPKVA
Consensus NRAVFkagQ# Nip!lKRdvA GDASESALLK CIELscGSVk .MR#Rn.K!a 151                                                         200
humana1   EIPFNSTNKY QLSIHKNPNT SEPQHLLVMK GAPERILDRC SSILLHGKEQ
humana3   EIPFNSTNKY QLSIHETEDP NDNRYLLVMK GAPERILDRC STILLQGKEQ
humana2   EIPFNSTNKY QLSIHERED. SPQSHVLVMK GAPERILDRC STILVQGKEI
Consensus EIPFNSTNKY QLSIHe.e#. s...hlLVMK GAPERILDRC StILlqGKEq 201                                                         250
humana1   PLDEELKDAF QNAYLELGGL GERVLGFCHL FLPDEQFPEG FQFDTDDVNF
humana3   PLDEEMKEAF QNAYLELGGL GERVLGFCHY YLPEEQYPQG FAFDCDDVNF
humana2   PLDKEMQDAF QNAYMELGGL GERVLGFCQL NLPSGKFPRG FKFDTDELNF
Consensus PLDeE$k#AF QNAY$ELGGL GERVLGFChl .LP.eq%P.G F.FDtD#vNF 251                                                         300
humana1   PIDNLCFVGL ISMIDPPRAA VPDAVGKCRS AGIKVIMVTG DHPITAKAIA
humana3   TTDNLCFVPL MSMIGPPRAA VPDAVGKCRS AGIKVIMVTG DHPITAKAIA
humana2   PTEKLCFVGL MSMIDPPRAA VPDAVGKCRS AGIKVIMVTG DHPITAKAIA
Consensus pt#nLCFVgL mSMIdPPRAA VPDAVGKCRS AGIKVIMVTG DHPITAKAIA 301                                                         350
humana1   KGVGIISEGN ETVEDIAARL NIPVSQVNPR DAKACVVHGS DLKDMTSEQL
humana3   KGVGIISEGN ETVEDIAARL NIPVSQVNPR DAKACVIHGT DLKDFTSEQI
humana2   KGVGIISEGN ETVEDIAARL NIPMSQVNPR EAKACVVHGS DLKDMTSEQL
Consensus KGVGIISEGN ETVEDIAARL NIPvSQVNPR #AKACV!HGs DLKDmTSEQl 351                                                         400
humana1   DDILKYHTEI VFARTSPQQK LIIVEGCQRQ GAIVAVTGDG VNDSPALKKA
humana3   DEILQNHTEI VFARTSPQQK LIIVEGCQRQ GAIVAVTGDG VNDSPALKKA
```

FIG. 20a

```
humana2    DEILKNHTEI VFARTSPQQK LIIVEGCQRQ GAIVAVTGDG VNDSPALKKA
Consensus  D#ILknHTEI VFARTSPQQK LIIVEGCQRQ GAIVAVTGDG VNDSPALKKA 401                                                446
humana1    DIGVAMGIAG SDVSKQAADM ILLDDNFASI VTGVEEGRLI FDNLKK
humana3    DIGVAMGIAG SDVSKQAADM ILLDDNFASI VTGVEEGRLI FDNLKK
humana2    DIGIAMGISG SDVSKQAADM ILLDDNFASI VTGVEEGRLI FDNLKK
Consensus  DIG!AMGIaG SDVSKQAADM ILLDDNFASI VTGVEEGRLI FDNLKK
```

Consensus symbols:
! is anyone of IV
$ is anyone of LM
% is anyone of FY
# is anyone of NDQEBZ

FIG. 20b

```
            1                                                            50
      Ha1   GTAGCCAATG TGCCGGAAGG TTTGCTGGCC ACTGTCACGG TCTGTCTGAC
      Ha2   GTGGCCAACG TGCCTGAGGG GCTTCTGGCC ACTGTCACTG TGTGCCTGAC
      Ha3   GTGGCCAATG TCCCAGAGGG TCTGCTGGCC ACTGTCACTG TGTGTCTGAC
Consensus   GTgGCCAAtG TgCC.GAgGG tcTgCTGGCC ACTGTCACtG TgTGtCTGAC 51                                                           100
      Ha1   ACTTACTGCC AAACGCATGG CAAGGAAAAA CTGCTTAGTG AAGAACTTAG
      Ha2   CCTGACAGCC AAGCGCATGG CACGGAAGAA CTGCCTGGTG AAGAACCTGG
      Ha3   CGTGACCGCC AAGCGCATGG CCCGGAAGAA CTGCCTGGTG AAGAACCTGG
Consensus   ccTgAC.GCC AAgCGCATGG CacGGAAgAA CTGCcTgGTG AAGAACcTgG 101                                                           150
      Ha1   AAGCTGTGGA GACCTTGGGG TCCACGTCCA CCATCTGCTC TGATAAAACT
      Ha2   AGGCGGTGGA GACGCTGGGC TCCACGTCCA CCATCTGCTC GGACAAGACG
      Ha3   AGGCTGTAGA GACCCTGGGC TCCACGTCCA CCATCTGCTC AGATAAGACA
Consensus   AgGCtGTgGA GACccTGGGc TCCACGTCCA CCATCTGCTC .GAtAAgAC.

151                                                           200
      Ha1   GGAACTCTGA CTCAGAACCG GATGACAGTG GCCCACATGT GGTTTGACAA
      Ha2   GGCACCCTCA CCCAGAACCG CATGACCGTC GCCCACATGT GGTTCGACAA
      Ha3   GGGACCCTCA CTCAGAACCG CATGACAGTC GCCCACATGT GGTTTGACAA
Consensus   GG.AccCTcA CtCAGAACCG cATGACaGTc GCCCACATGT GGTTtGACAA 201                                                           250
      Ha1   TCAAATCCAT GAAGCTGATA CGACAGAGAA TCAGAGTGGT GTCTCTTTTG
      Ha2   CCAAATCCAT GAGGCTGACA CCACCGAAGA TCAGTCTGGG GCCACTTTTG
      Ha3   CCAGATCCAC GAGGCTGACA CCACTGAGGA CCAGTCAGGG ACCTCATTTG
Consensus   cCAaATCCAt GAgGCTGAcA CcAC.GAggA tCAGtctGGg gcCtCtTTTG 251                                                           300
      Ha1   ACAAGACTTC AGCTACCTGG CTTGCTCTGT CCAGAATTGC AGGTCTTTGT
      Ha2   ACAAACGATC CCCTACGTGG ACGGCCCTGT CTCGAATTGC TGGTCTCTGC
      Ha3   ACAAGAGTTC GCACACCTGG GTGGCCCTGT CTCACATCGC TGGGCTCTGC
Consensus   ACAAgagtTC .cctACcTGG .tgGCcCTGT CtcgaATtGC tGGtCTcTGc 301                                                           350
      Ha1   AACAGGGCAG TGTTTCAGGC TAACCAGGAA AACCTACCTA TTCTTAAGCG
      Ha2   AACCGCGCCG TCTTCAAGGC AGGACAGGAG AACATCTCCG TGTCTAAGCG
      Ha3   AATCGCGCTG TCTTCAAGGG TGGTCAGGAC AACATCCCTG TGCTCAAGAG
Consensus   AAccGcGC.G TcTTcaAGGc tgg.CAGGA. AACaTccCtg TgcttAAGcG 351                                                           400
      Ha1   GGCAGTTGCA GGAGATGCCT CTGAGTCAGC ACTCTTAAAG TGCATAGAGC
      Ha2   GGACACAGCT GGTGATGCCT CTGAGTCAGC TCTGCTCAAG TGCATTGAGC
```

FIG. 21a

```
         Ha3 GGATGTGGCT GGGGATGCGT CTGAGTCTGC CCTGCTCAAG TGCATCGAGC
   Consensus GGa.gt.GCt GG.GATGCcT CTGAGTCaGC .CTgcTcAAG TGCAT.GAGC 401                                             450
         Ha1 TGTGCTGTGG TTCCGTGAAG GAGATGAGAG AAAGATACGC CAAAATCGTC
         Ha2 TCTCCTGTGG CTCAGTGAGG AAAATGAGAG ACAGAAACCC CAAGGTGGCA
         Ha3 TGTCCTCTGG CTCCGTGAAG CTGATGCGTG AACGAAACAA GAAAGTGGCT
   Consensus gTcCTgTGG cTCcGTGAaG .agATGaGaG AaaGAaAC.c cAAagTgGc.

451                                             500
         Ha1 GAGATACCCT TCAACTCCAC CAACAAGTAC CAGTTGTCTA TTCATAAGAA
         Ha2 GAGATTCCTT TCAACTCTAC CAACAAGTAC CAGCTGTCTA TCCACGAGCG
         Ha3 GAGATTCCCT TCAATTCCAC CAACAAATAC CAGCTCTCCA TCCATGAGAC
   Consensus GAGATtCCcT TCAAcTCcAC CAACAAgTAC CAGcTgTCtA TcCAtgAGa.

501                                             550
         Ha1 CCCCAACACA TCGGAGCCCC AACACCTGTT GGTGATGAAG GGCGCCCCAG
         Ha2 AGAAGACAGC CCCCAGAGCC ...ACGTGCT GGTGATGAAG GGGGCCCCAG
         Ha3 CGAGGACCCC AACGACAACC GATACCTGCT GGTGATGAAG GGTGCCCCCG
   Consensus cga.gACacc .ccgAga.CC .a.ACcTGcT GGTGATGAAG GG.GCCCCaG 551                                             600
         Ha1 AAAGGATCCT AGACCGTTGC AGCTCTATCC TCCTCCACGG CAAGGAGCAG
         Ha2 AGCGCATTCT GGACCGGTGC TCCACCATCC TGGTGCAGGG CAAGGAGATC
         Ha3 AGCGCATCCT GGACCGCTGC TCCACCATCC TGCTACAGGG CAAGGAGCAG
   Consensus AgcGcATcCT gGACCG.TGC tcCaCcATCC TgcT.CAgGG CAAGGAGcag 601                                             650
         Ha1 CCCCTGGATG AGGAGCTGAA AGACGCCTTT CAGAACGCCT ATTTGGAGCT
         Ha2 CCGCTCGACA AGGAGATGCA AGATGCCTTT CAAAATGCCT ACATGGAGCT
         Ha3 CCTCTGGACG AGGAAATGAA GGAGGCCTTT CAGAATGCCT ACCTTGAGCT
   Consensus CC.CTgGAcg AGGAgaTGaA aGA.GCCTTT CAgAAtGCCT Ac.TgGAGCT 651                                             700
         Ha1 GGGGGGCCTC GGAGAACGAG TCCTAGGTTT CTGCCACCTC TTTCTGCCAG
         Ha2 GGGGGGACTT GGGGAGCGTG TGCTGGGATT CTGTCAACTG AATCTGCCAT
         Ha3 CGGTGGCCTG GGCGAGCGCG TGCTTGGTTT CTGCCATTAT TACCTGCCCG
   Consensus gGGgGGcCT. GG.GAgCG.G TgCT.GGtTT CTGcCA.ct. tatCTGCCag 701                                             750
         Ha1 ATGAACAGTT TCCTGAAGGG TTCCAGTTTG ACACTGACGA TGTGAATTTC
         Ha2 CTGGAAAGTT TCCTCGGGGC TTCAAATTCG ACACGGATGA GCTGAACTTT
         Ha3 AGGAGCAGTA TCCCCAAGGC TTTGCCTTCG ACTGTGATGA CGTGAACTTC
   Consensus atGaacAGTt TCCtcaaGGc TTc.a.TTcG ACactGAtGA .gTGAAcTTc
```

FIG. 21b

```
              751                                                          800
      Ha1   CCTATCGATA ATCTGTGCTT TGTTGGGCTC ATCTCCATGA TTGACCCTCC
      Ha2   CCCACGGAGA AGCTTTGCTT TGTGGGGCTC ATGTCTATGA TTGACCCTCC
      Ha3   ACCACGGACA ACCTCTGCTT TGTGCCGCTC ATGTCCATGA TCGGCCCACC
Consensus   cCcAcgGA.A A.CT.TGCTT TGTgggGCTC ATgTCcATGA TtGacCCtcc 801                                                          850
      Ha1   ACGGGCGGCC GTTCCTGATG CCGTGGGCAA ATGTCGAAGT GCTGGAATTA
      Ha2   CCGGGCTGCT GTGCCAGATG CTGTGGGCAA GTGCCGAAGC GCAGGCATCA
      Ha3   CCGGGCAGCC GTCCCTGACG CGGTGGGCAA GTGTCGCAGC GCAGGCATCA
Consensus   cCGGGC.GCc GT.CCtGAtG C.GTGGGCAA gTGtCGaAGc GCaGGcATcA 851                                                          900
      Ha1   AGGTCATCAT GGTCACAGGA GACCATCCAA TCACAGCTAA AGCTATTGCC
      Ha2   AGGTGATCAT GGTAACCGGG GATCACCCTA TCACAGCCAA GGCCATTGCC
      Ha3   AGGTCATCAT GGTCACCGGC GATCACCCCA TCACGGCCAA GGCCATTGCC
Consensus   AGGTcATCAT GGTcACcGG. GAtCAcCC.A TCACaGCcAA gGCcATTGCC 901                                                          950
      Ha1   AAAGGTGTGG GCATCATCTC AGAAGGCAGT GGACCTATGA GCAGAGGAAA
      Ha2   AAAGGCGTGG GCATCATATC AGAGGGTAAC GAGACTGTGG AGGACATTGC
      Ha3   AAGGGTGTGG GCATCATCTC TGAGGGCAAC GAGACTGTGG AGGACATCGC
Consensus   AAaGGtGTGG GCATCATcTC aGAgGGcAac GagaCTgTGg aggacat.gc 951                                                         1000
      Ha1   ATCGTGGAGT TCACCTGCCA CACAGCCTTC TTCGTCAGTA TCGTGGTGGT
      Ha2   AGCCCGGC.T CAACATTCCC ATGAGTCAA. ...GTCA...A CCCCAGAGAA
      Ha3   CGCCCGGC.T CAACATTCCC GTCAGCCAG. ...GTTA...A CCCCCGGGAT
Consensus   agCccGGc.T caACaTtCCc .tcAGcCa.. ...GTcA...A cCcc.G.Gat 1001                                                         1050
      Ha1   GCAGTGGGCC GACTTGGTCA TCTG.TAAGA CCAGGAGGAA TTCGGTCTTC
      Ha2   GCCAAGG.CA TGCGTGGTGC ACGGCTCTGA CCTGAAGGAC ATGA..CATC
      Ha3   GCCAAGG.CC TGCGTGATCC ACGGCACCGA CCTCAAGGAC TTCA..CCTC
Consensus   GCcaaGG.Cc tgCgTGgTcc aCgGctc.GA CCtgaAGGAc tTca...C.TC 1051                                                         1100
      Ha1   CAGCAGGGGA TGAAGAACAA GATCTTGATA TTTGGCCTCT TTGAAGAGAC
      Ha2   G.....GAGC AGCTCGATGA GATCCTCAAG AACCACACAG AGATCGTCTT
      Ha3   C.....GAGC AAATCGACGA GATCCTGCAG AATCACACCG AGATCGTCTT
Consensus   c.....GaGc agatcgAcgA GATCCtgaag aatcaCaccg agatcGtctt 1101                                                         1150
      Ha1   AGCCCTGGCT GCTTTCCTTT CCTACTGCCC TGGAATGGGT GTTGCTCTTA
```

FIG. 21c

```
       Ha2  TGCTCGAACG TCTCCCCAGC AGAAGCTCAT CATTGTGGAG GGATGTCAGA
       Ha3  CGCCCGCACA TCCCCCCAGC AGAAGCTCAT CATTGTGGAG GGCTGTCAGA
 Consensus  .GCcCg.aC. tCtccCCagc agaAgctCat cattgTGGag Gg.tgTCagA 1151                                               1200
       Ha1  GGATGTATCC CCTCAAACC. .TACCTGGTG GTTCTGTGC. CTTCCCCTAC
       Ha2  GGCAGGGAGC CATTGTGGCC GTGACGGGT  ACGGGGTGAA CGACTCCCCT
       Ha3  GACAGGGTGC AATTGTGGCT GTGACCGGGG ATGGTGTGAA CGACTCCCCC
 Consensus  GgcaGggtgC caTtgtggC. gTgaC.GGtG atggtGTGaa CgaCtCCccc 1201                                               1250
       Ha1  TCTCTTCTCA TCTTCGTATA TGACGAAGTC A..GAAAACT CATCATCAGG
       Ha2  GCATTGAAGA AGGCTGACAT TGGCATTGCC ATGGGCATCT CTGGCTCTGA
       Ha3  GCTCTGAAGA AGGCCGACAT TGGGGTGGCC ATGGGCATCG CTGGCTCTGA
 Consensus  gCtcTgaagA aggccGacat TGgcgt.GcC AtgGgcAtCt CtggcTCtGa 1251                                               1300
       Ha1  CGACGCC... CTGGCGGCTG GGTGGA.... GAAGGAAACC TACTATTAGC
       Ha2  CGTCTCTAAG CAGGCAGCCG ACATGATCCT GCTGGATGAC AACTTTGCCT
       Ha3  CGTCTCCAAG CAGGCAGCTG ACATGATCCT GCTGGACGAC AACTTTGCCT
 Consensus  CGtCtCcaag CaGGCaGCtG acatGAtcct GctGGA.gaC aACTtTgcct 1301                                               1350
       Ha1  CCCCCGTCCT GCACGCCGTG GAGCATCAGG CCACACACTC TGCATCCGAC
       Ha2  CCATCGTCAC GGGGGTGGAG GAGGGCC..G CCTGATCTTT GACAACTTGA
       Ha3  CCATCGTCAC AGGGGTGGAG GAGGGCC..G CCTGATCTTC GACAACCTAA
 Consensus  CCatCGTCac ggggGtgGaG GAGggcC..G CCtgAtctTc gaCAaCctaa 1351
       Ha1  ACCCA
       Ha2  AGAAA
       Ha3  AGAAG
 Consensus  Agaaa Consensus symbols:
 ! is anyone of IV
 $ is anyone of LM
 % is anyone of FY
 # is anyone of NDQEBZ
```

FIG. 21d

IGE-DEPENDENT HISTAMINE-RELEASING FACTOR-BINDING PEPTIDES

TECHNICAL FIELD

The present invention relates to IgE-dependent histamine-releasing factor (hereinafter, abbreviated as "HRF") receptor, HRF-binding peptides and nucleic acids encoding the same, and uses thereof. More specifically, the present invention relates to novel receptors against HRF causing allergic diseases such as asthma, rhinitis, urticaria, anaphylaxis, allergic bronchiectasis, allergies due to foods, drugs, pollen, insects, etc., hay fever, cold urticaria or atopic dermatitis, HRF-binding peptides and nucleic acid encoding the same, and uses thereof in the medicinal area.

BACKGROUND ART

Allergies are known as being caused by inheritable hypersensitive formation of IgE in response to allergens, or disruption of balance between IL-4 (Interleukin-4) increasing IgE secretion and interferon decreasing IgE secretion. Upon the exposure to allergens, an immediate reaction occurs and various cells associated with inflammation are gathered, and after several hours, late-phase reaction (hereinafter, abbreviated as "LPR") occurs by histamine and other cytokines secreted from basophils, eosinophils and lymphocytes. In LPR, histamine is secreted from basophils, but allergens, which have initiated the reaction, do not exist any longer. Further, LPR is developed in only about half of patients suffered from allergies. Therefore, what causes histamine secretion from basophils and what causes development into LPR have been issues of great interest. To the present time, cytokines such as MCP-3, MCP-1 or RANTES were known as secreting histamine. But, it was found that in IgE-dependent LPR, only HRF can induce histamine secretion from basophils (MacDonald, et al., 1995), the mechanism of which has never been known.

HRF, which is a ubiquitous cytoplasmic protein, is a known protein consisting of 172 amino acids (Bohm, et al., 1989). 45 Amino acids at its C-terminal form basic domain. Because such domain has about 46% homology with MAP-1B, microtubule-associated protein, it was assumed that HRF is also microtubule-associated protein. Gachet, et al. (1997) observed that HRF is distributed consistently with the cytoskeletal network to some extent by using confocal microscope, which suggests that HRF binds to the cytoskeleton. Meanwhile, Sanchez, et al. (1997) published that HRF, even though it does not fall within general $Ca^{2+}$-binding protein family, binds to $Ca^{2+}$ and further, identified that yeast cells can survive with the deletion of HRF genes in *Saccharomyces cerevisiae*. These suggest that HRF falls within the gene family having redundant pathway. MacDonald, et al. (1995) also found HRF, which is an intracellular protein, in the outside of cells. Further, it was known that HRF present in the outside of cells stimulates IgE-sensitized basophils to release histamine, but an accurate interaction between IgE and HRF has not been identified (Schroeder, et al., 1996). Schroeder, et al. (1997) observed that HRF can augment the anti-IgE-induced histamine release from all basophils, regardless of the IgE type, and thus suggested that HRF exerts its function by binding to cell membrane receptors, not by binding with IgE. Accordingly, the followings have been important issues, i.e. how HRF is secreted to the outside of cells and how it stimulates IgE-sensitized basophils to release histamine. Since HRF, a hydrophilic and intracellular protein, is detected in LPR allergy patients plasma at a large amount, it was assumed to be secreted to the outside of cells by apoptosis or other mechanisms and to release histamine via HRF receptors present in basophil membrane. In addition, because this HRF exists in most of tissues, it is assumed to function in tissue cells other than in inflammatory cells. But, its functions in other tissues than inflammatory cells, particularly in cerebral tissue or nerve cells, have never been reported. Recently, HRF was found during the analysis of proteins present in human brain using 2-D gel electrophoresis and proteomics (Langen, et al., 1999). Subsequently, it was also reported that HRF protein is decreased in the brain of patients died of Down's syndrome or Alzheimer's disease (Kim, et al., 2001).

On the other hand, (Na,K)ATPase, which involves in the formation of resting membrane potential and in the balanced regulation of osmosis within cells, is also present in nerve cells, particularly nerve end or synaptosomal membranes, at a high concentration and plays an important role in neuro-activity. It was reported that in case of inhibition or loss of (Na,K)ATPase activity in nerve cell membrane, various neuropathological changes or apoptosis occurs (Lees, 1991). This is also related to the report that the intracellular ATP essential for (Na,K)ATPase activity is rapidly exhausted in cerebral ischemia or anoxia state (Martin, et al., 1994; Santos, et al., 1996). Therefore, it is believed that this enzyme activity is also inhibited in such cerebral disease states. Moreover, it was confirmed that in rat brain tissue slices, synaptosomes and in vitro culture system, in case (Na,K)ATPase activity is inhibited, neurotransmitters release is increased. From other in vivo and in vitro studies, it was suggested that neurotransmitters release is increased in ischemia or anoxia-like conditions and the resulting activation of postsynaptic cell membrane receptors is an important procedure in nerve injury (Choi, 1990; Martin, et al., 1994).

Cerebral (Na,K)ATPase activity is regulated not only by neurotransmitters such as dopamine, serotonin, norepinephrine, glutamate, etc. but also by endogenous substances such as insulin, nitric oxide (NO), etc. An endogenous (Na,K)ATPase inhibitor named "brain ouabain", which is structurally similar to ouabain, glycoside extracted from plants, was identified (Budzikowski, et al., 1998). But, Rodriguez, et al. (1992) reported that there exists an endogenous ouabain-like factor specifically inhibiting (Na,K)ATPase activity in soluble brain fractions and having the different structure and properties from ouabain. They also reported that it blocks high affinity $^3$H-ouabain binding to induce neurotransmitters release, and involves in (Na,K)ATPase activity regulation by neurotransmitters as well. Recently, that substance was named endobain E (Vatta, et al., 1999), bur has not yet been identified.

DISCLOSURE OF THE INVENTION

Surprisingly, the present inventors found that HRF, even though it is a hydrophilic protein, can transit the cell membrane and HRF receptor corresponds to a third cytoplasmic domain (CD3) of (Na,K)ATPase by yeast two-hybrid assay. In addition, the inventors first identified an accurate mechanism by which extracellularly secreted HRF stimulates histamine release within basophils.

Further, on the basis of the results as described above, the inventors anticipated that any allergic diseases can be effectively prevented or treated by blocking HRF introduction into the cells and/or HRF binding with (Na,K)ATPase to inhibit histamine release. Therefore, they have performed extensive studies on peptides binding to HRF by screening 12 mer and 7 mer phage display libraries and as a result, obtained peptides of the specific sequences which can inhibit histamine secretion at a remarkably high rate and thus, completed the present invention.

Accordingly, an object of the present invention is to provide novel HRF receptors, peptide binding to HRF and uses thereof.

A first aspect of this invention relates to a rat HRF receptor having the amino acid sequence selected from SEQ ID No. 1, 2 or 3.

A second aspect thereof relates to a human HRF receptor having the amino acid sequence selected from SEQ ID No. 4, 5 or 6.

A third aspect thereof relates to a HRF receptor having the sequence homology of 85% or more with any one of the above amino acid sequences.

The HRF receptor may be a large cytoplasmic loop [CD (cytoplasmic domain) 3] of (Na,K)ATPase α1, α2 or α3 subunit.

A fourth aspect of this invention relates to a nucleic acid encoding any one of the above HRF receptors. The nucleic acid may have the nucleotide sequence selected from SEQ ID No. 7, 8 or 9 (rat HRF), or selected from SEQ ID No. 10, 11 or 12 (human HRF).

A fifth aspect thereof relates to a recombinant vector comprising the above nucleic acid.

A sixth aspect thereof relates to a cell transformed with the above vector.

A seventh aspect thereof relates to a screening method of HRF receptor-interactive compounds, which comprises contacting the transformed cells with test compounds and compounds known as interacting with the receptors, and then, selecting compounds decreasing the interaction of the known compounds from the test compounds (competition binding assay).

A eighth aspect of the present invention relates to a HRF-binding peptide having the amino acid sequence as represented by the following formula:

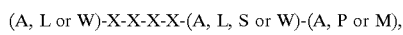

(A, L or W)-X-X-X-X-(A, L, S or W)-(A, P or M), wherein X represents any amino acid.

Preferably, the HRF-binding peptide in accordance with the invention has the amino acid sequence (A, L or W)-X-X-(Y, P or A)-(P, G or K)-(A, L, S or W)-(A, P or M).

More preferably, it has the amino acid sequence (A, L or W)-(V, Y, E or A)-(T, V, F or A)-(Y, P or A)-(P, G or K)-(A, L, S or W)-(A, P or M), exemplified by any one of SEQ ID Nos. 13 to 22.

Still more preferably, it has the amino acid sequence (A or W)-(Y or A)-(V or A)-(Y or A)-(P or K)-(S or A)-(M or A), for example, of SEQ ID No. 14, 16, 17, 18, 19, 20, 21 or 22.

Most preferably, it has the amino acid sequence W-(Y or A)-(V or A)-(Y or A)-(P or K)-(S or A)-M, for example, of SEQ ID No. 14, 17, 18, 19, 20 or 21.

Such RF-binding peptide may be composed of L-, D-, or L- and D-amino acids, and contain one or more modified amino acids, for example, amino acid derivatives or alkylated, particularly methylated, amino acids.

A ninth aspect of the present invention relates to a nucleic acid encoding the HRF binding peptide.

A tenth aspect thereof relates to a recombinant vector comprising the nucleic acid.

A eleventh aspect thereof relates to a cell transformed with the recombinant vector.

A twelfth aspect thereof relates to a composition for diagnosis, prophylaxis or treatment of allergies, particularly asthma, rhinitis, urticaria, anaphylaxis, allergic bronchiectasis, allergies due to foods, drugs, pollen, insects, etc., hay fever, cold urticaria, or atopic dermatitis. The composition comprises as an active ingredient the HRF-binding peptide or the nucleic acid encoding the same.

A thirteenth aspect thereof relates to an agent inducing the release of neurotransmitters, e.g. dopamine, comprising as an active ingredient HRF or the nucleic acid encoding the same.

A fourteenth aspect thereof relates to an agent inhibiting the release of neurotransmitters, e.g. dopamine, in particular, for diagnosis, prophylaxis or treatment of apoptosis-associated nerve diseases such as cerebral apoplexy, Alzheimer's disease or Parkinson's disease. The agent comprises as an active ingredient the BRF-binding peptide or the nucleic acid encoding the same.

A fifteenth aspect thereof relates to a composition for diagnosis, prophylaxis or treatment of malaria, comprising as an active ingredient the HRF-binding peptide or the nucleic acid encoding the same.

Hereinafter, the present invention will be explained in detail.

The present inventors first identified that HRF binds to large cytoplasmic loop (CD3) in (Na,K)ATPase α subunit by using yeast 2-hydrid assay. The inventors also found that HRF interacts with CD3 in (Na,K)ATPase α subunit by coimmunoprecipitation in yeast and mammalian cells and measured their binding affinity. Further, they confirmed that HRF receptor is CD3 in (Na,K)ATPase α subunit under confocal microscope.

Additionally, they demonstrated that HRF, a water-soluble protein, can enter the cells by confocal microscope and Western blotting, and identified that it increases the intracellular $Na^+$ and $Ca^{2+}$ concentrations and thus, the extracellular $Ca^{2+}$ sources are consumed by Na/Ca exchanger. They also found that in the presence of IgE, BRF generates ROS (reactive oxygen species), which results in the inflow of much more $Ca^{2+}$ to the cells.

From the above-described facts, an accurate mechanism by which HRF stimulates histamine release from basophils has been revealed. That is, extracellularly secreted HRF enters the basophils and binds to CD3 of (Na,K)ATPase α subunit and then, inhibits (Na,K)ATPase activity like ouabain thereby to increase intracellular $Na^+$ and $Ca^{2+}$ concentrations following the activation of Na/Ca exchanger. Further, in the presence of IgE, intracellular $Ca^{2+}$ is further increased due to the generation of ROS, which ultimately stimulates histamine release. This means that HRF receptor is CD 3 of (Na,K)ATPase and HRF is a cytoplasmic repressor of (Na,K)ATPase.

Accordingly, the identity of HRF receptor was first revealed by the present inventors and thus, in the present invention, provided is a HRF receptor having the amino acid sequence of SEQ ID No 1, 2 or 3. This receptor corresponds to CD3 in α1, α2 or α3 subunit of (Na,K)ATPase isolated from rat. But, as long as the fact that HRF receptor corresponds to CD3 in a subunit of (Na,K)ATPase (Na,K)ATPase has been discovered by the present inventors, any person having an ordinary skill in the art can easily identify human HRF receptors. Therefore, human HRF receptors also fall within the scope of the present invention, which have the amino acid sequence of SEQ ID No 4 (α1), 5 (α2) or 6 (α3).

In rat (Na,K)ATPase, the sequence homology between α1 and α2 CD3 is 87.6%, and that between α2 and α3 CD3 is 89.4%. In CD3 of (Na,K)ATPase α subunits, the sequence homology between rat and human is 97.5% in α1, 99.3% in α2 and 98.8% in α3, respectively (see FIGS. 18 to 21). Accordingly, the present invention provides HRF receptors having the sequence homology of 85% or more with any of the amino acid sequences of SEQ ID Nos. as set forth above.

This invention provides nucleic acids encoding the HRF receptors, for example, having the nucleotide sequences selected from any one of SEQ ID Nos. 7 (rat α1), 8 (rat α2) and 9(rat α3), or any one of SEQ ID Nos. 10 (human α1), 11 (human α2) and 12 (human α3). In addition, provided are recombinant vectors comprising the above-described nucleic acids and cells transformed with the recombinant vectors as well.

This invention also provides a screening method of compounds interacting with HRF receptor, characterized by using the above-described cells in competition binding analysis. In the competition binding assay, the cells transformed with the recombinant vector containing the nucleic acid encoding HRF receptor and HRF protein are contacted with test compounds and compounds, which were already known as interacting with the receptor. Then, compounds which inhibit the interaction of the known compounds are selected among the above test compounds. The above method enables the screening of novel compounds, which can effectively regulate histamine release within cells.

Moreover, the invention provides peptides inhibiting histamine release by binding to HRF with a high specific affinity. In one embodiment, provided are peptides having the amino acid sequence of the following formula:

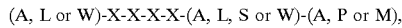

(A, L or W)-X-X-X-X-(A, L, S or W)-(A, P or M), wherein X represents any amino acid.

Examples of HRF-binding peptides include the followings:

(A, L or W)-X-X-(Y, P or A)-(P, G or K)-(A, L, S or W)-(A, P or M);

particularly, (A, L or W)-(V, Y, E or A)-(T, V, F or A)-(Y, P or A)-(P, G or K)-(A, L, S or W)-(A, P or M), e.g. SEQ ID Nos. 13, 14, 15, 16, 17, 18, 19, 20, 21 or 22;

more particularly, (A or W)-(Y or A)-(V or A)-(Y or A)-(P or K)-(S or A)-(M or A), e.g. SEQ ID Nos. 14, 16, 17, 18, 19, 20, 21 or 22; and, most particularly, W-(Y or A)-(V or A)-(Y or A)-(P or K)-(S or A)-M, e.g. SEQ ID Nos. 14, 17, 18, 19, 20 or 21.

The present inventors obtained the above peptides by phage displayed library screening and then, repeated experiments using synthetic peptides. The peptides in accordance with this invention may be chemically synthesized or prepared using genetic recombination technology. Preferably, domains composing the peptides may be prepared from proteins in vivo or parts thereof. The peptides may be prepared by recombinant DNA technology using expression vectors to which DNA encoding the peptides is inserted. The vector is prepared to be targeted in vivo, and appropriate host cells are transformed therewith and then, cultured to expression under a suitable condition according to the method of Sambrook, et al. (Molecular Cloning, 1989, Cold Spring Harbor, Cold Spring Harbor Laboratory Press). Also, the peptides may be prepared by use of fusion proteins containing the amino acid sequence according to the present invention.

In the present invention, the amino acid sequences of the peptides can be varied according to any conventional method known in the art. For example, the peptides can be varied by changing the number of amino acids. The peptides are also varied by substitution or conversion of specific residues except those directly involving in the binding or having to be conserved, within the scope of not deteriorating the activity of the peptides. The amino acids may be modified not only to naturally occurring L-α-amino acids but also to D-α-amino acids as well as β, γ or δ-amino acids.

Typically, as a result of analyzing the effects of electrostatic force or hydrophilicity on binding, the sensitivity is likely to be changed in case of substitution of positively-charged amino acids, e.g. Lys, Arg, His, or negatively-charged amino acids, e.g. Glu, Asp, Asn, Gln. As mentioned above, kind and number of residues that can be substituted or added are determined depending upon required space between the essential binding points and required functions such as hydrophilicity or hydrophobicity. By such substitution, the affinity of the peptides with target proteins can be further increased.

Substitution may accompany critical functional alterations. The selection of residues for substitution may greatly affect basic skeletal structures of the peptides by changing their electricity, hydrophobicity, or side chains or helical structures, etc. Variations greatly affecting properties of peptides, are exemplified by substitution of hydrophilic residues, e.g. serine, with hydrophobic residues, e.g. leucine, isoleucine, phenylalanine, valine or alanine, substitution of positively-charged residues, e.g. lysine, arginine or histidine, with negatively-charged residues, e.g. glutamic acid or aspartic acid, or substitution of residues having no side chain, e.g. glycine, with residues having bulky side chain.

Considering the above-described facts, the skilled person in the art can modify the specific peptides by using any conventional method within the scope of maintaining or enhancing, or not deteriorating the binding affinity with HRF and inhibitory activity on histamine release. This is construed to fall within the scope of the present invention.

The peptides of the present invention is useful in the diagnosis, prophylaxis or treatment of any HRF-associated allergic diseases, e.g. asthma, rhinitis, urticaria, anaphylaxis, allergic bronchiectasis, allergies due to foods, drugs, pollen, insects, etc., hay fever, cold urticaria, or atopic dermatitis. Since HRF is commonly detected in the blood of patients suffered from the above allergic diseases (see FIG. 22), the skilled person can easily anticipate that the peptides of the present invention are effective in diagnosis, prophylaxis or treatment of the above exemplified allergic diseases.

Accordingly, the invention provides a composition for prophylaxis or treating allergies comprising as an active ingredient the above peptides. The peptides can be administered with a daily dose of about 0.1~5 mg, preferably, 0.3~2.5 mg, per body weight of 1 kg. The present composition may be formulated into solutions or micelles and then, directly injected to human or animals. The composition can be applied by parenteral or topical administrations, preferably by intravenous, subcutaneous, endothelial or muscular injection. For this purpose, the peptides are dissolved or suspended in pharmaceutically acceptable carriers, particularly, in water-soluble carriers.

Further, the peptides of the present invention may be contained in a diagnosis kit of allergies. The diagnosis kit may comprise the HRF-binding peptides and anti-HRF monoclonal antibodies. In the test using the present kit, in case of positive blood reaction, it is decided that the subject is afflicted by allergies even in the absence of allergens. That is, since HRF is floating in the blood of LPR allergy patients, it can be determined whether or not HRF is present in the blood by use of the present kit, thereby to distinguish LPR patients. In one embodiment, the HRF-binding peptides are attached to the bottom of a container, reacted with a blood sample and then, conjugated anti-HRF monoclonal antibodies are added thereto.

Moreover, the present inventors examined whether or not HRF increases neurotransmitters release by inhibitory activity on (Na,K)ATPase in nerve cells. For this purpose, HRF is added to the culture solution of nerve cell line, art-known PC12 cells (Abu-Raya, et al., 1999), which contain secretory granules of neurotransmitters and thus, are particularly suitable for studying the regulation of catecholamine release, to measure changes in [$^3$H]-labeled dopamine release. As a result, the inventors found that in PC12 cells, HRF dose-dependently increases basal and K$^+$-stimulated releases in a depolarized state induced by the increase of K$^+$. They also confirmed that the HRF-binding peptides effectively block neurotransmitters release induced by HRF in nerve cells.

As set forth above, HRF, which involves in the intracellular regulation of (Na,K)ATPase activity, stimulates neurotransmitters release by inhibitory activity on (Na,K) ATPase playing an important role in neuroactivity in nerve cells and therefore, is believed to play an important role in pathophysiological effects in nerve cells as well as brain. For this reason, the HRF-binding peptides capable of blocking the increase in neurotransmitters release by HRF are extremely useful for diagnosis, prophylaxis or treatment of various apoptosis-associated nerve diseases, e.g. cerebral apoplexy, Alzheimer's disease, Parkinson's diseases, etc. Therefore, according to the present invention, provided is a composition for diagnosis, prophylaxis or treatment of various apoptosis-associated nerve diseases, e.g. cerebral apoplexy, Alzheimer's disease, Parkinson's diseases, etc. In this case, the administration routes and dosages as mentioned above can be also applied.

Meanwhile, HRF is also called translationally controlled tumor protein. It was already known that an anti-malaria agent Artemisinin binds to malaria protein HRF (Bhisutthibhan, et al., 1998). Therefore, the peptides of the invention having the binding affinity with HRF can be employed in prophylaxis or treatment of malaria in the same manner as Artemisinin. In this case, the administration routes and dosages as mentioned above can be also applied.

BRIEF DESCRIPTION OF THE DRAWINGS

FIGS. 18a and 18b show the amino acid sequences conserved between rat HRF receptors;

FIGS. 19a to 19d show the nucleotide sequences conserved between DNA encoding rat HRF receptors;

FIGS. 20a and 20b show the amino acid sequences conserved between human HRF receptors;

FIGS. 21a to 21d show the nucleotide sequences conserved between DNA's encoding human HRF receptors;

BEST MODE FOR CARRYING OUT THE INVENTION

This invention will be better understood from the following examples. However, one skilled in the art will readily appreciate the specific materials and results described are merely illustrative of, and are not intended to, nor should be intended to, limit the invention as described more fully in the claims, which follow thereafter.

EXAMPLE 1

Identification of the HRF Binding to (Na,K)ATPase Large Cytoplasmic Loop by Yeast 2-hybrid Analysis The total cytoplasmic RNA was extracted from rat skeletal muscle and then, cDNA library for yeast 2-hybrid analysis was constructed by using pJG4–5 vector. CD3 region of (Na,K)ATPase α2 subunit was inserted to LexA DNA binding domain (pEG202 vector) and the inserts were used as bait for screening. Positive clones activating reporter gene were selected and sequence analyzed by sequencing, restriction mapping and BLAST search. Among those clones, one clone had the completely identical sequence with HRF.

CD3 regions of (Na,K)ATPase α1 and 2 subunits were inserted to pEG202 vector and then, the interaction by isoforms was examined. Yeast cells containing LexAop-LEU2 and LexAop-LacZ reporter genes (EGY48/pSH18–34) were transformed with all the constructs as prepared above and then, grown in a selective medium plate.

Figure 1:
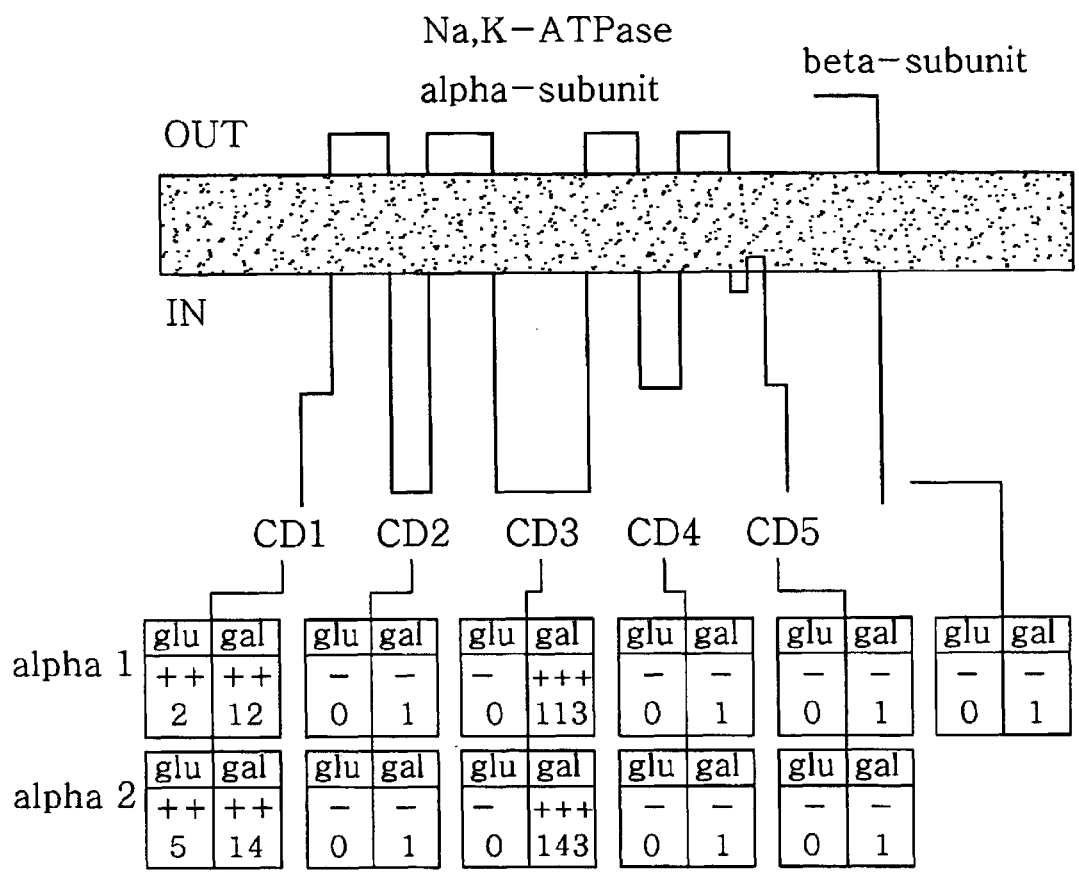
FIG. 1 shows the results of yeast 2-hydrid analysis identifying that HRF receptor is (Na,K)ATPase large cytoplasmic loop.

The results are shown in FIG. 1. From FIG. 1, it can be seen that HRF receptor corresponds to large cytoplasmic loop (CD3) of (Na,K)ATPase.

EXAMPLE 2

Identification of Interaction between HRF and (Na, K)ATPase by Coimmunoprecipitation in Yeast and COS-7 Cells In Glucosyl Ura-His-Trp- and galactosyl Ura-His-Trp-media, yeast cells transformed with the constructs prepared in Example 1 were grown, and the cells were harvested by centrifugation at 3,000×g for 5 minutes. The harvested cells were resuspended in yeast lysis buffer (YLB: 50 mM Tris pH 8.0, 5 mM $MgCl_2$, 150 mM NaCl, 50 mM NaF, 2 mM $ZnCl_2$, protease inhibitor cocktail) and subsequently, the suspension was added to glass beads and vortexed. Thereto was added RIPA buffer (10 mM Tris pH 8.0, 100 mM NaCl, 1 mM EDTA, 1% $NP_4O$, 0.5% sodium deoxycholate, 0.1% SDS) and then, the whole mixture was centrifuged at 10,000×g, 4° C. for 30 minutes.

Figure 2:
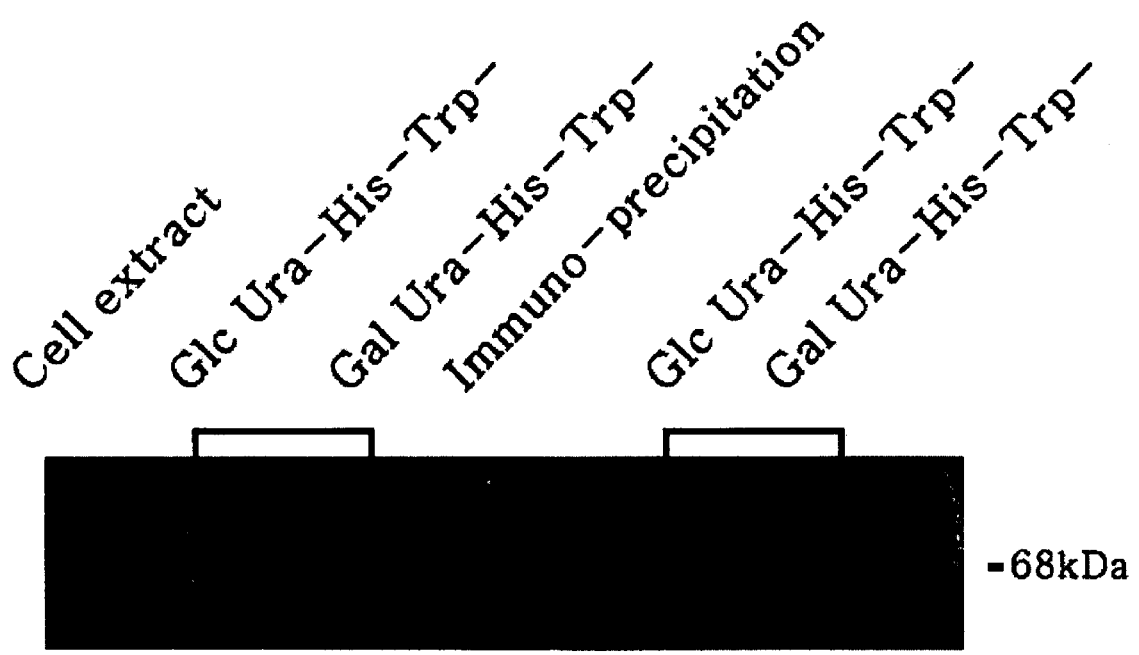
FIG. 2 shows the results of coimmunoprecipitation in yeast cells identifying that HRF is interacted with (Na,K) ATPase large cytoplasmic loop.

To the cell extracts as prepared above, IgG sorb (The Enzyme Center, Inc.) was added and then, the mixture was incubated at 4° C. for 30 minutes and centrifuged at 10,000×g for 5 minutes. Thereto was added affinity-purified anti-HA 12CA5 monoclonal antibodies and then, the resulting mixture was incubated for 3 hours or overnight at 4° C. 50% protein A agarose solution (Roche, USA) was added to the above immunocomplex and the whole mixture was incubated at 4° C. for 4 hours. After centrifugation for 5 seconds, the obtained pellets were washed with RIPA buffer and washing buffer (1 M NaCl, 10 mM Tris pH 8.0, 0.1% $NP_4O$), respectively. The pellets were resuspended in 2×SDS sample buffer and then, the suspension was loaded onto SDS-PAGE gel. To detect the interactive proteins, rabbit polyclonal LexA antibodies were added thereto. The results are shown in FIG. 2 and from this, the interaction between HRF and (Na,K)ATPase large cytoplasmic loop could be confirmed.

Figure 3:
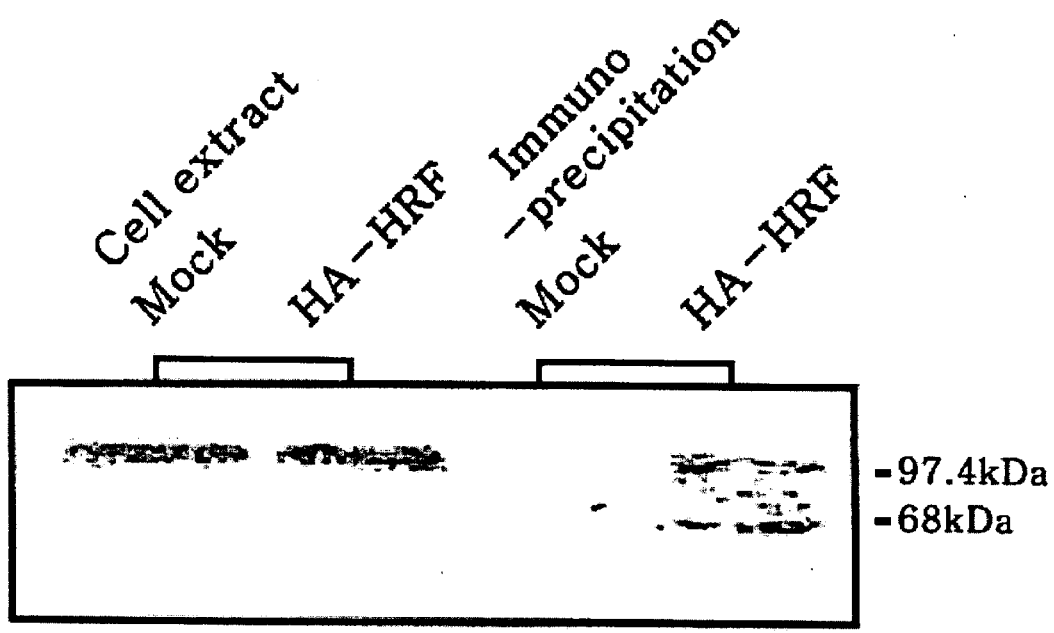
FIG. 3 shows the results of coimmunoprecipitation in COS-7 cells identifying that HRF is interacted with (Na,K) ATPase large cytoplasmic loop.

Subsequently, to examine such interaction in mammalian cells, COS-7 cells were grown in $DMEM^+$ culture (Dulbeccos modified Eagles medium containing 10% fetal bovine serum, 100 units/ml penicillin and 100 units/ml streptomycin). The cells were transfected with N-terminal HA-tagged HRF constructs inserted to pCDNAneo vector (Invitrogen). COS-7 cell extracts were immunoprecipitated according to the method of Florkiewicz, et al. (1998). To detect the interactive protein, rabbit polyclonal anti-(Na,K) ATPase antibodies were added thereto. The results are shown in FIG. 3. As shown in FIG. 3, HRF was also interacted with (Na,K)ATPase large cytoplasmic loop in the mammalian COS-7 cells.

EXAMPLE 3

Figure 4:
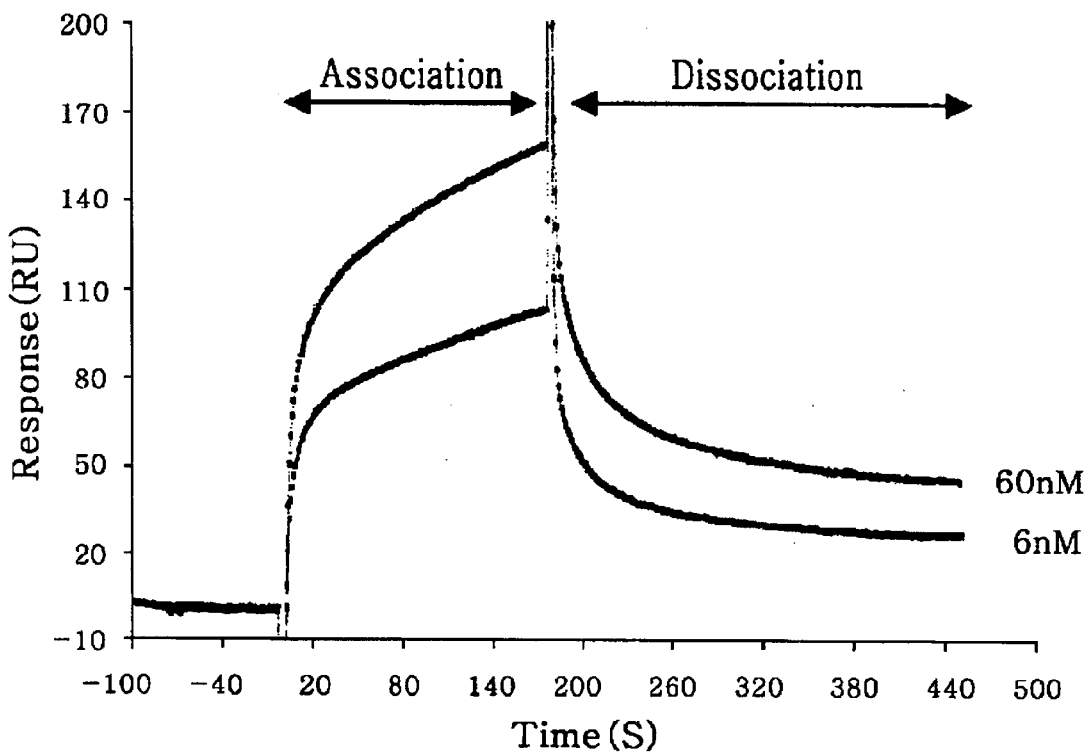
FIG. 4 is a graph which shows the results of measuring the binding affinity of HRF with (Na,K)ATPase large cytoplasmic loop by Biacore method.

Measurement of the Binding Affinity of HRF with (Na,K)ATPase by Biacore Analysis Recombinant rat HRF was immobilized on CM5 sensor chip at a concentration of 10 mg/ml in pH 4.0, 10 mM acetate and then, corrected by flowing HBS buffer (0.01 M Hepes, pH 7.4, 0.15 M NaCl, 3 mM EDTA, 0.005% surfactant P20). Subsequently, it was activated by flowing 50 mM NHS (N-hydroxysuccinimide) and 200 mM EDC(N-ethyl-N-(3-diethylaminopropyl)carbodiimide). The binding affinity was measured by flowing (Na,K)ATPase. The results are shown in FIG. 4 and the $K_d$ value was $8.5 \times 10^{-7}$ M.

EXAMPLE 4

Figure 5:
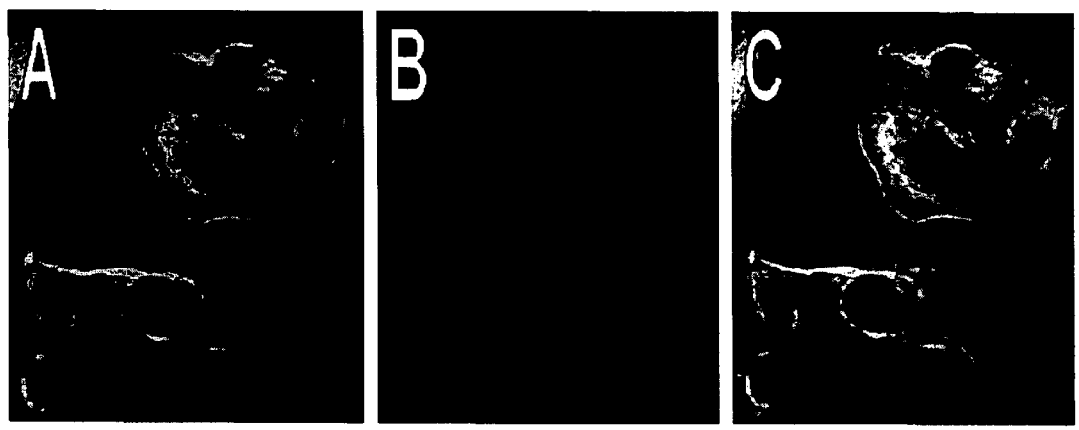
FIGS. 5A–5C is a confocal microscopic photograph identifying that HRF receptor is (Na,K)ATPase large cytoplasmic loop.

Identification of Interaction between HRF and (Na, K)ATPase by Confocal Microscope COS-7 cells were immobilized with 3.7% formaldehyde containing $Ca^{2+}$ and $Mg^{2+}$ for 10 minutes and then, stained with mouse anti-HRF monoclonal antibodies (1:100) (provided from Ewha Womans University Antibody Center) and/or rabbit anti-(Na,K)ATPase polyclonal antibodies (1:100) containing 0.1% saponin at room temperature for 1 hour. Subsequently, the cells were incubated with anti-mouse-FITC (1:100) and anti-rabbit-rhodamine (1:100) secondary antibodies for 30 minutes. Anti-bleaching agent solution was added thereto and then, observation was made under laser confocal microscope (Leica TCSNT system). The results are shown in FIG. 5.

EXAMPLE 5

Measurement of HRF's Capability of Transiting Cell Membrane

The full-length rat HRF sequence (Chitpatima, et al., 1988) amplified by PCR (polymerase chain reaction) was cloned in pRSET-A vector and then, overexpressed in *E. coli*. The expressed recombinant protein was purified by His-bound Ni column (Novagen) and then, added to COS-7 cell culture solution. COS-7 cells were immobilized with 3.7% formaldehyde containing $Ca^{2+}$ and $Mg^{2+}$ for 10 minutes. Then, the cells were stained with anti-His monoclonal antibodies (1:100) containing 0.1% saponin at room temperature for 1 hour. Subsequently, they were incubated with anti-mouse-FITC (1:100) secondary antibodies for 30 minutes. Anti-bleaching agent solution was added thereto and then, observation was made under laser confocal microscope (Leica TCSNT system).

Further, COS-7 cells cultivated in 100 mm culture plate were treated according to the above method. Then, the cells were divided into cytoplasmic fraction and cell membrane fraction. They were loaded onto 10% SDS-PAGE gel and then, Western blotting was carried out using anti-His monoclonal antibodies.

Figure 6A:
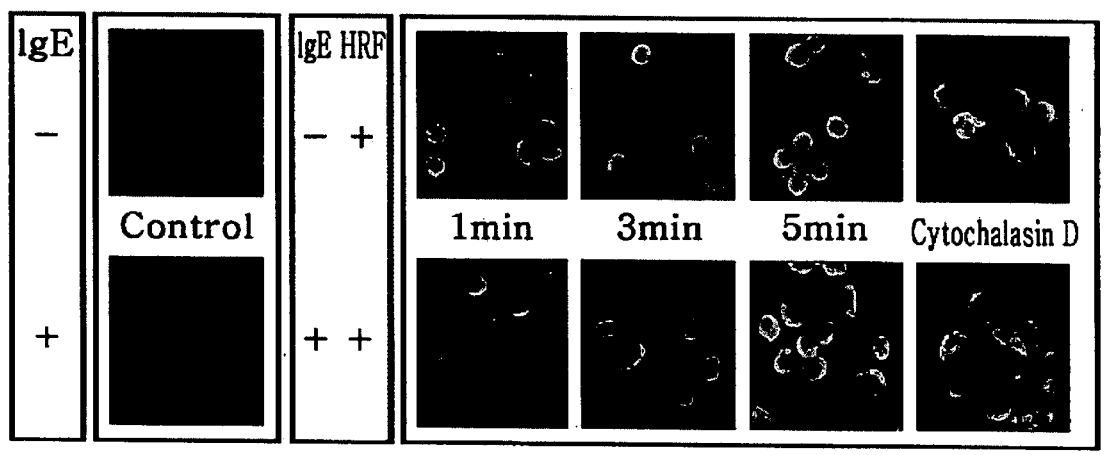
FIGS. 6a and 6b are photographs showing the results of confocal microscopy and Western blotting identifying that the water-soluble protein HRF can enter the cells.
Figure 6B:
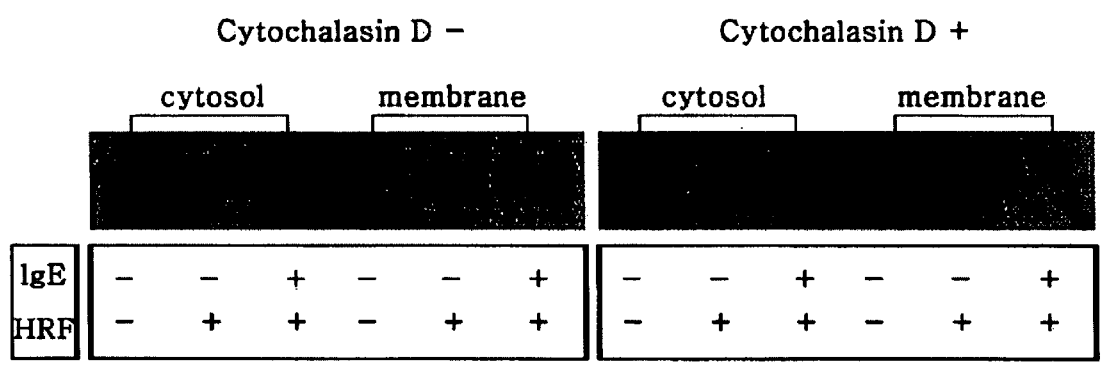

The results are shown in FIGS. 6a and 6b. As shown in the figures, HRF was detected within the cells at 1 minute after its addition.

EXAMPLE 6

Analysis of Effects on Intracellular $Na^+$ Concentration by HRF

RBL-2H3 cells were loaded onto 24-well plate at $3.0 \times 10^5 \sim 1 \times 10^6$ cells/ml and cultivated at 37° for 18 hours. Hams F-12 culture (phenol red or serum-free 2 mM sodium bicarbonate and 10 mM HEPES, pH 7.3) was mixed with sodium green tetracetate dye (Molecular Probes, Eugene, Oreg.) at a final concentration of 8 M and the mixture was loaded onto the cells (Amorino and Fox, 1995). The cells were sensitized with 0.2 µg/ml of rat IgE (Serotec) for 45~60 minutes and then, cultivated at room temperature for about 20~60 minutes and washed three times with F-12 medium.

Figure 7:
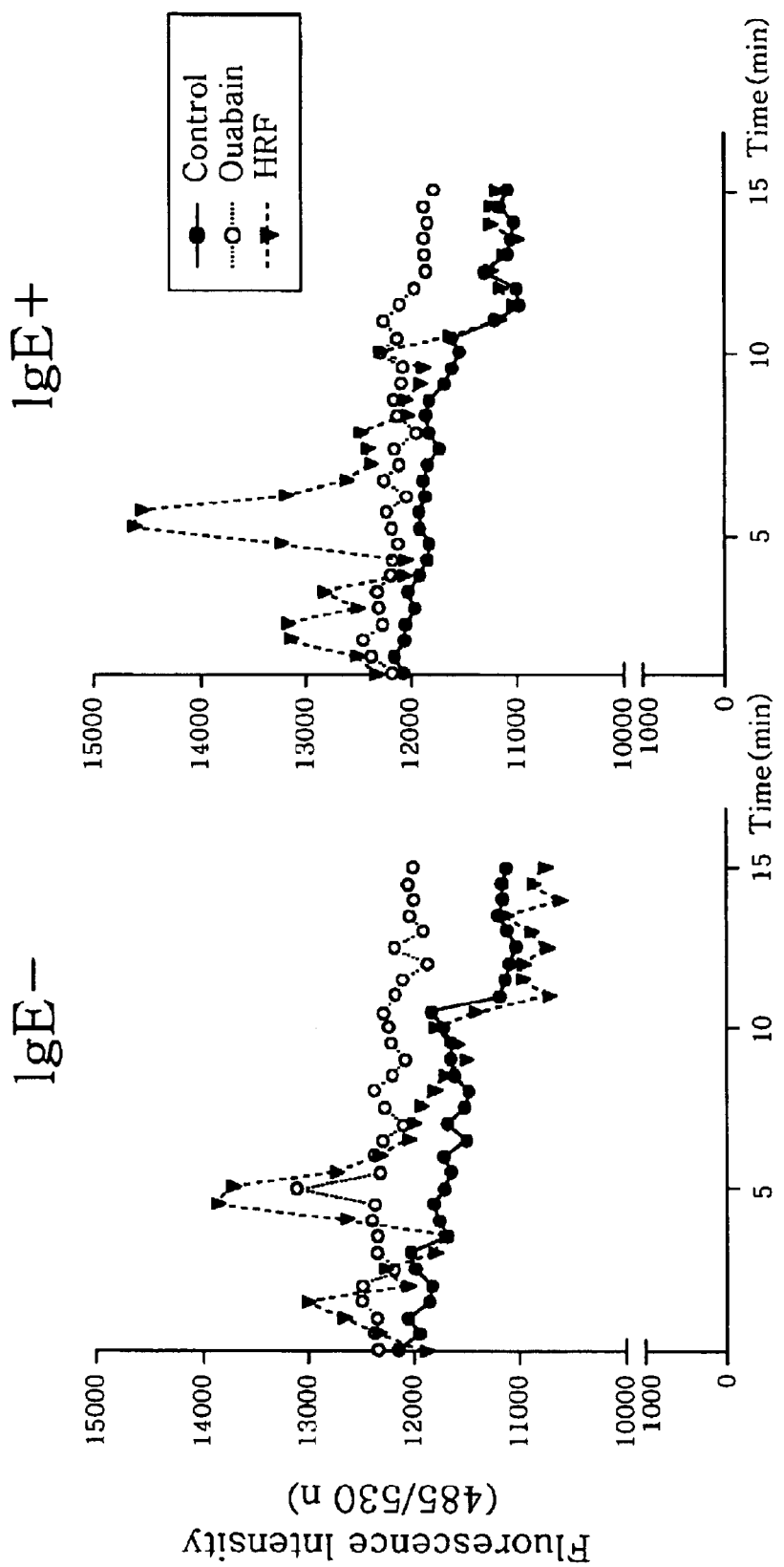
FIG. 7 is a graph showing the increase in intracellular Na$^+$ concentration by HRF.

Subsequently, thereto was added HRF (10~20 μg/ml) in histamine releasing buffer and then, fluorescence was measured with microtiter reader (FL600, Bio-tek Instruments, Inc., Winooski, Vt.) at 485/530 nm for 15 minutes. The mixed solution of $Na^+$ and $K^+$ at an appropriate concentration was measured using gramicidin D (Sigma) as calibration (Amorino and Fox, 1995). The results are shown in FIG. 7. As shown in FIG. 7, HRF increased the intracellular $Na^+$ concentration.

EXAMPLE 7

Measurement of Inhibitory Activity on (Na,K) ATPase by HRF

Figure 8:
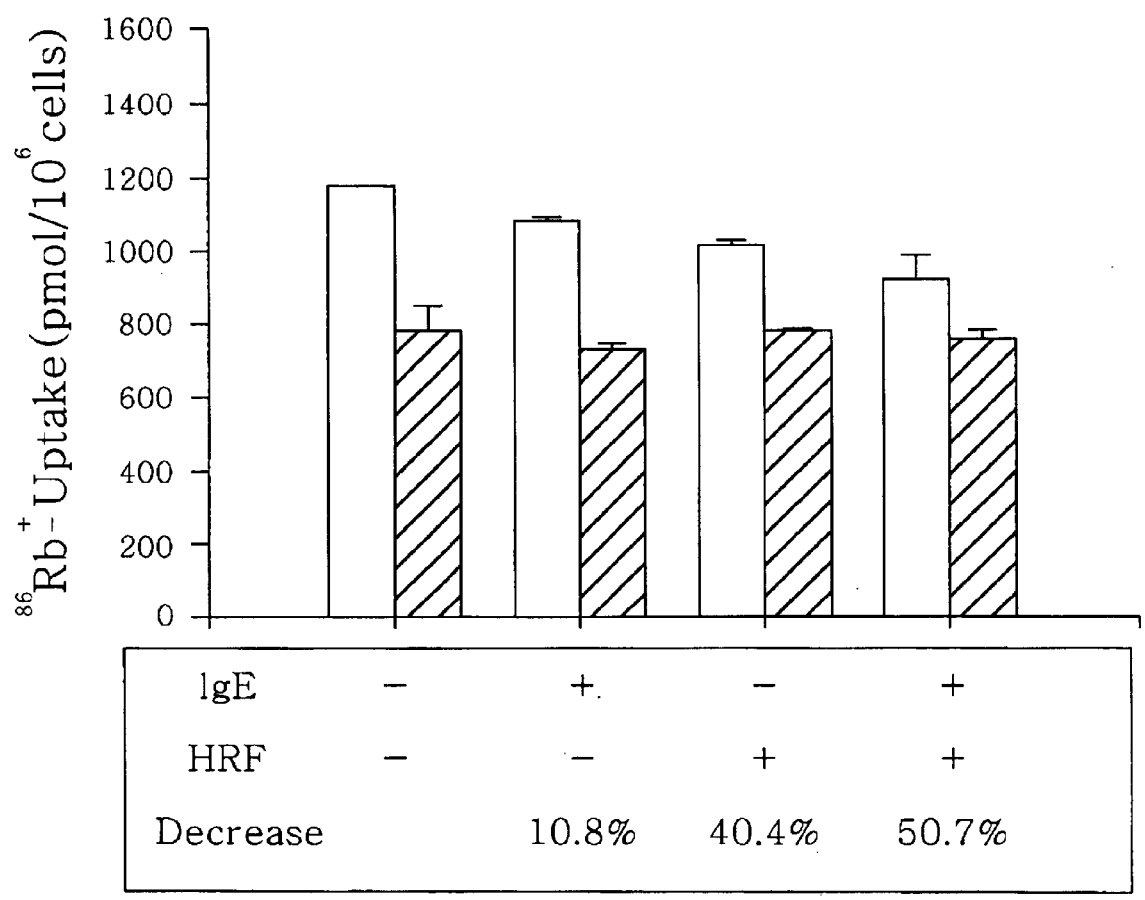
FIG. 8 is a graph showing the decrease in (Na,K)ATPase activity by HRF.

RBL-2H3 cells were cultivated and sensitized according to the same procedures as in Example 6 and then, washed three times with Krebs-Ringer buffer (KRP, 140 mM NaCl, 5 mM KCl, 10 mM $Na_2HPO_4$, 1 mM $MgSO_4$, 1.4 mM $CaCl_2$, 2.5 mM glucose, pH 7.4). Subsequently, the cells were incubated at 37° C. for 15 minutes and then, thereto was added 0.1% bovine serum albumin (BSA)-containing KRP buffer comprising 1 mM ouabain. $^{86}Rb^+$(0.5 Ci/ml, NEN) was used as a tracer and the cells were cultivated for 5~10 minutes. 10~20 g/ml HRF was added thereto and $K^+$-uptake was measured for 5, 10 and 15 minutes, respectively. The results are shown in FIG. 8. As shown in FIG. 8, HRF decreased the (Na,K)ATPase activity by 10.8%, 40.4% and 50.7% respectively.

EXAMPLE 8

Analysis of Effects on Intracellular $Ca^{2+}$ Concentration by HRF

Figure 9A:
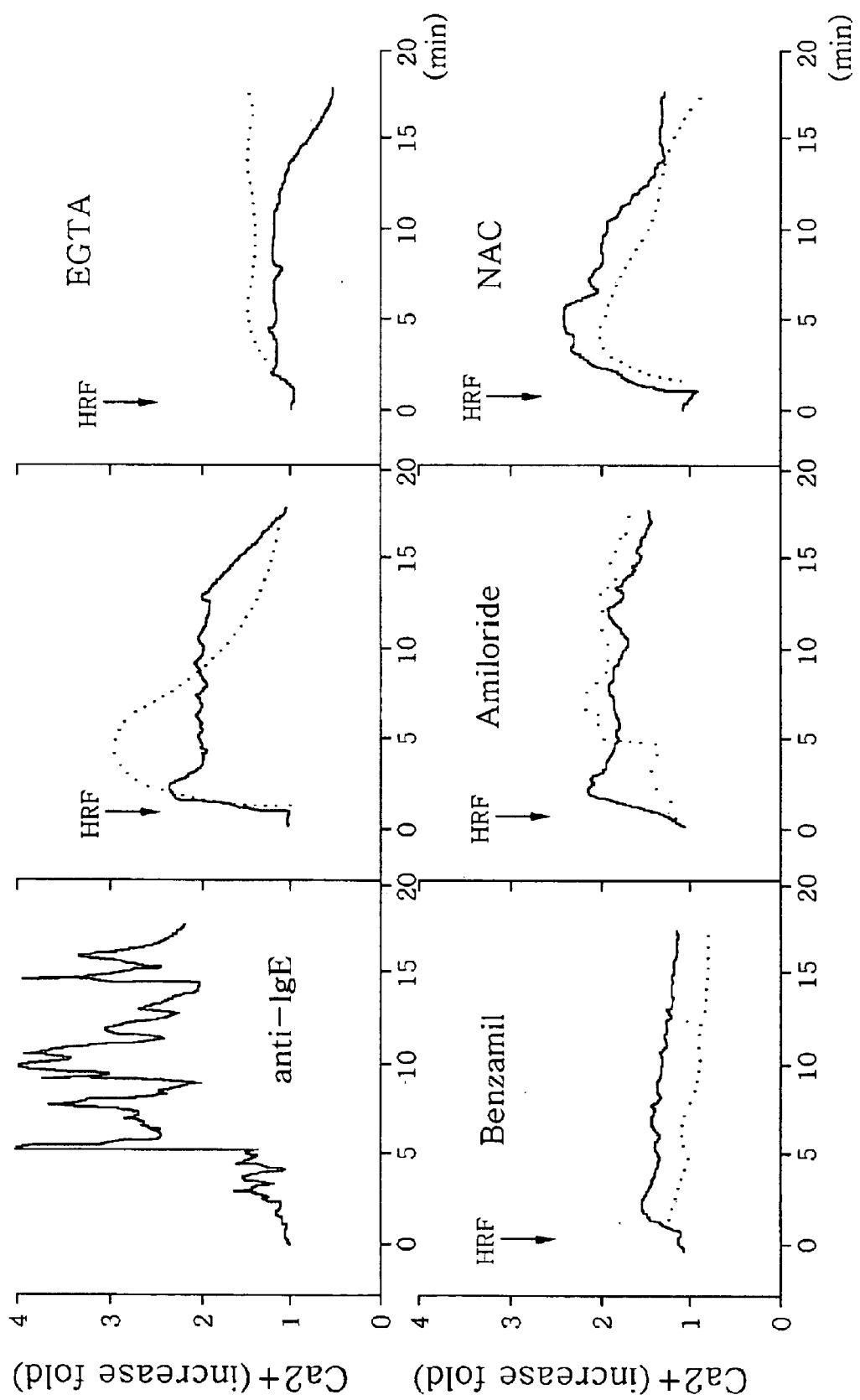
FIGS. 9a to 9c are graphs showing the increase in intracellular Ca$^{2+}$ concentration by HRF, increase in extracellular Ca$^{2+}$ source uptake by Na/Ca exchanger and further increase in intracellular Ca$^{2+}$ concentration by ROS generation in the presence of IgE.

RBL-2H3 cells were cultivated according to the same procedure as in Example 6 and then, washed with Krebs-Ringer buffer (KRH, 125 mM NaCl, 1.2 mM $KH_2PO_4$, 1.2 mM $MgSO_4$, 6 mM glucose, 2 mM $CaCl_2$, 25 mM Hepes, pH 7.4). Subsequently, they were incubated with 2 μM Fluo-3-AM (Molecular Probes, Eugene, Oreg.) and KRH buffer containing 0.2% BSA for 30 minutes and then, the culture was corrected with DMEM complete medium for 10~30 minutes. Subsequently, the cells were washed with KRH buffer and sensitized according to the same procedure as in Example 6. After the sensitization, the cells were treated with HRF, anti-IgE (Serotec) and each inhibitor together with histamine releasing buffer (100 mM NaCl, 0.4 mM $MgCl_2$, 5 mM KCl, 5.6 mM glucose, 0.1% BSA, 25 mM Hepes, pH 7.4) in the presence or absence of $Ca^{2+}$. The fluorescence of fluo-3AM was measured at 488/515 nm using laser scanning confocal microscope. The results are shown in FIG. 9a.

Intracellular ROS was measured with laser scanning confocal microscope using 2',7'-dichlorofluorescein diacetate (DCFH-DA). That is, RBL-2H3 cells were cultivated in complete DMEM medium in the presence or absence of IgE for 1 hour. Subsequently, they were washed with Krebs-Ringer solution and then, cultured in Krebs-Ringer solution containing 5 μM DCFH-DA for 5 minutes. The cells were observed while scanning fluorescence at 488/515 nm. The results are shown in FIGS. 9b and 9c.

Figure 9B:
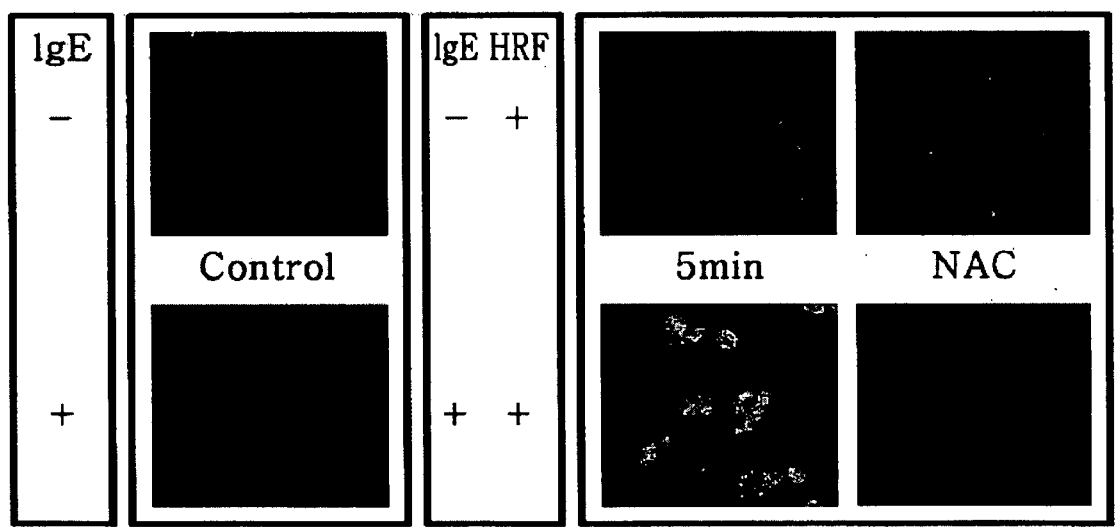
Figure 9C:
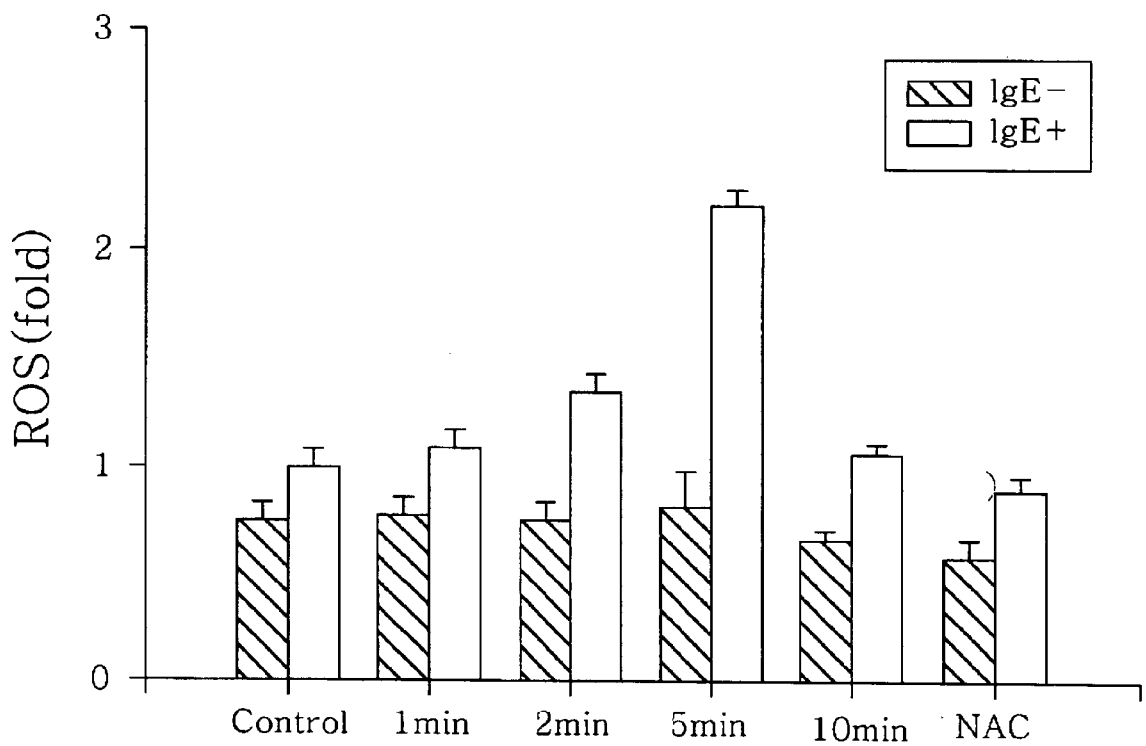

As described above, the intracellular $Ca^{2+}$ concentration was increased by HRF and simultaneously, the extracellular $Ca^{2+}$ was consumed by Na/Ca exchanger (FIG. 9a), and in the presence of IgE, ROS was formed and therefrom, the intracellular $Ca^{2+}$ was further increased (FIGS. 9b and 9c).

EXAMPLE 9

Figure 10:
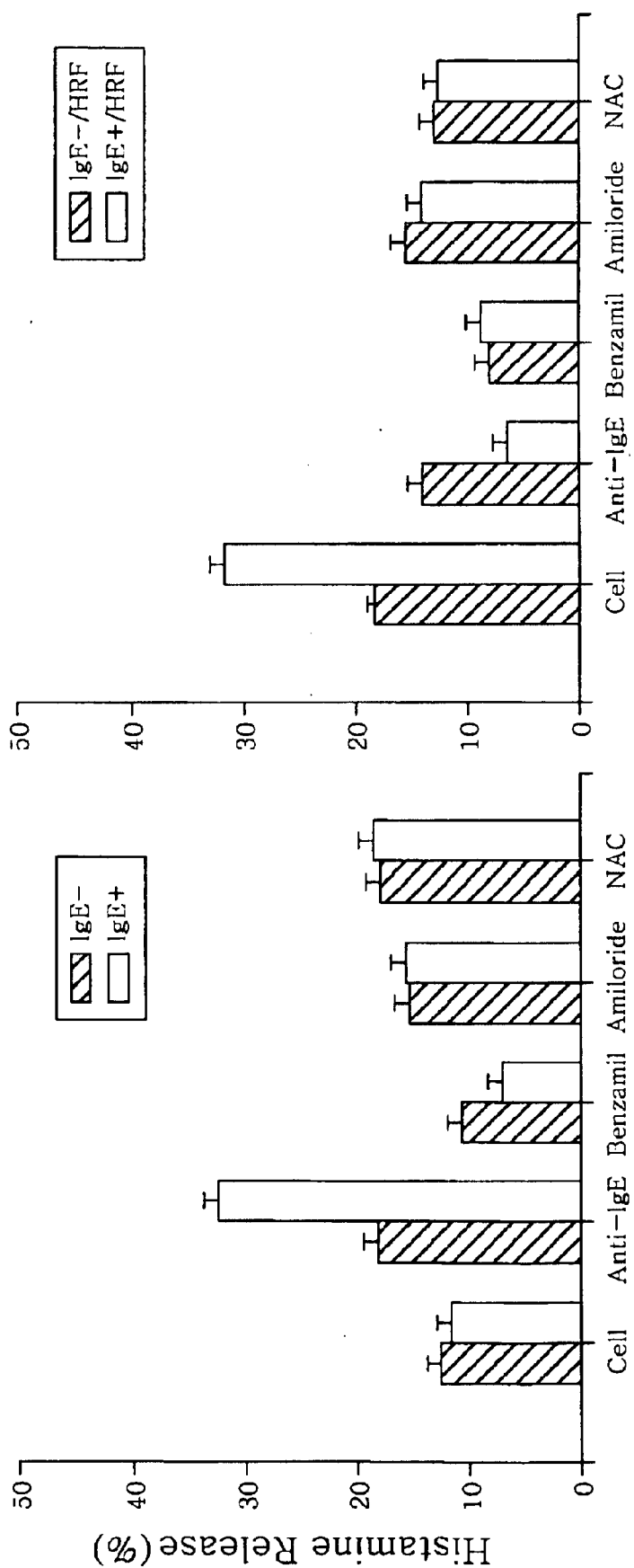
FIG. 10 is a graph showing histamine release by HRF with the increase in intracellular Ca$^{2+}$ concentration in the presence of IgE.

Identification of the Relationship between Increase in $Ca^{2+}$ Concentration by HRF and Histamine Release The full-length rat HRF sequence amplified by PCR was cloned in pRSET-A vector and then, overexpressed in *E. coli*. The expressed recombinant protein was purified using His-bound Ni column (Novagen) and used for stimulation of RBL-2H3 cells. RBL-2H3 cells were grown in 24-well plate at 1×10⁶ cells, sensitized with rat IgE antibody (0.2 μg/ml, Serotec) for 45~60 minutes and treated with 20 μg/ml of the recombinant HRF protein and the inhibitors as used above, respectively. The obtained sample was prepared to acylated histamine using RIA-analysis kit (Immunotech, France) and competitively bound to $^{125}I$-acylated histamine and monoclonal antibodies. The sample was analyzed by γ-counter. The results are shown in FIG. 10. As shown in FIG. 10, histamine was released by HRF with the increase in intracellular $Ca^{2+}$ concentration in the presence of IgE.

EXAMPLE 10

Isolation of Phage Displayed Peptide Clones Binding to HRF

HRF was immobilized in wells and HRF-binding peptides were isolated by affinity selection on HRF-heptamer random repeat peptide library (New England Biolabs, USA).

Briefly, 20 μg/ml of HRF in a coating buffer (0.1 M $NaHCO_3$, pH8.6) was added to a polystyrene microtiter plate at a volume of 50 μl and the plate was coated with HRF at 4° C. overnight. Non-specific binding was blocked with BSA and the plate was washed six times with 0.1% Tween/TBS (TBST). A solution prepared by diluting 10 μl of phage-displayed peptide library solution in 40 μl of 3% BSA/TBS was added thereto and the mixture was allowed to stand. After 5 minutes, it was washed with TBST, once in the 1st panning, five times in the 2nd and 3rd pannings and ten times in the 4th panning, respectively. 50 μl of glycine/HCl buffer (pH 2.2) was added thereto and the resulting mixture was placed for 5 minutes to elute the phages. The eluate was neutralized with 8 μl of 1 M Tris-HCl (pH 9.1).

Figure 11:
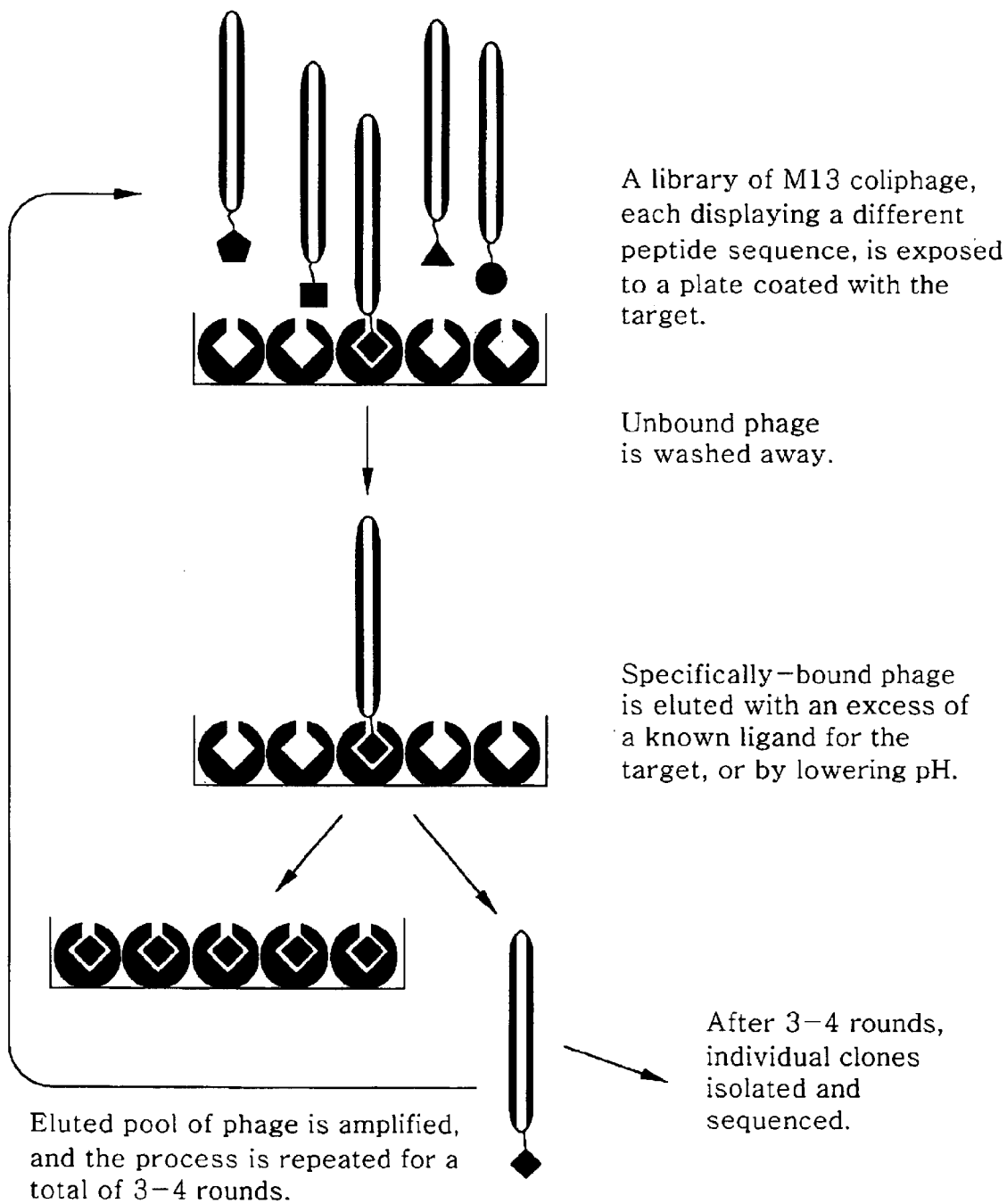
FIG. 11 is a schematic diagram, which illustrates the isolation procedure of genes encoding HRF-binding peptides.

The eluted phage solution was added to 20 ml of ER2537 culture solution ($OD_{600}$32 0.5~1) and cultured in 37° C. shaking incubator (rpm=200) for 2 hours. Then, 100 ml of SB medium was added thereto and the phage was cultured overnight at 250 rpm. The culture solution was centrifuged at 10,000 rpm (4° C.) for 5 minutes and to 100 ml of the supernatant was added 30 ml of 5×PEG/NaCl (20% PEG (w/v), 15% NaCl (w/v)) to dissolution for 5 minutes. The solution was then allowed to stand in an ice bath for 30 minutes and centrifuged at 10,000 rpm (4° C.) for 20 minutes. The supernatant was completely eliminated therefrom and the pellets were suspended in 1 ml of 3% BSA/TBS. Then, the supernatant obtained by centrifugation at 14,000 rpm for 5 minutes was used in the subsequent panning. The affinity purification and phage cloning were repeated 4 times and each phage clone was obtained from the titration plate of the eluted phages. Only the phage clones having the specific affinity in ELISA analysis were sequenced to identify the amino acid sequences. Isolation procedure of the genes encoding the HRF-binding peptides is schematically depicted in FIG. 11. In addition, the phage displayed peptides having the preferential binding to HRF are set forth in the following Table 1.

TABLE 1

| Phage | Peptide | Amino acid sequence | Frequency |
|---|---|---|---|
| ph1 | p1 | LVTYPLP | 1 |
| ph2 | p2 | WYVYPSM | 18 |
| ph3 | p3 | SYLPYPY | 1 |
| ph4 | p4 | WEFPGWM | 5 |

EXAMPLE 11

Phage ELISA

The binding affinities of the phages obtained from Example 10 were compared by ELISA as follows.

That is, the phage plaques were transferred to 1 ml of ER2537 culture solution cultivated in SB medium (OD$_{600}$= 0.5~1) and then, cultured in 37° C. incubator (rpm=250) for 5 hours. Each 100 μl of the culture solution was added to 900 μl of SB medium and cultured overnight. The culture solution was centrifuged twice at 14,000 rpm for 5 minutes per centrifugation and the obtained supernatant was used for ELISA.

Figure 12:
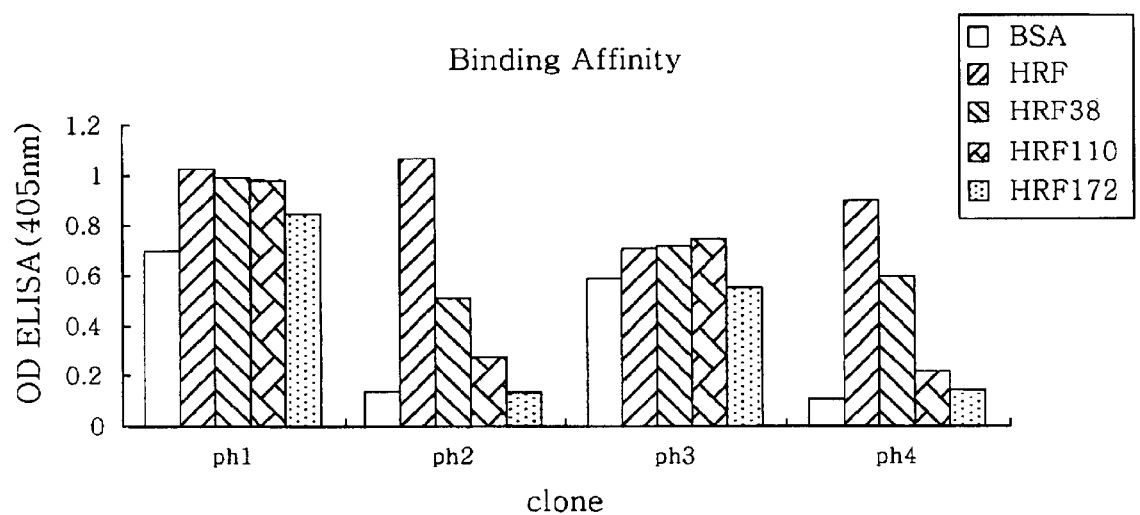
FIG. 12 is a graph showing the specific binding of peptides encoded by the phages with HRF.

To plastic wells, each of which was coated with HRF or BSA (control), 50 μl of a solution obtained by diluting each isolated phage solution with the equivalent amount of 6% BSA/PBS, and the resulting mixture was allowed to stand for 2 hours. After washing five times with PBST, 100 μl of HRP-conjugated anti-M13 antibodies (Pharmacia) diluted in 3% BSA/PBS with the ratio of 1:5000 were added thereto and the whole was allowed to stand for 1 hour. After washing six times with PBST and then, once with PBS, 100 μl of peroxydase substrate solution was added thereto. The chromogenicity was measured using ELISA reader at 405 nm. The results are shown in FIG. 12. From FIG. 12, it can be seen that the phages ph1, ph2 and ph4, especially ph2 and ph4, specifically bind to HRF.

EXAMPLE 12

Measurement of Dose-dependent Binding Affinity of HRF with Phage Clones

Figure 13:
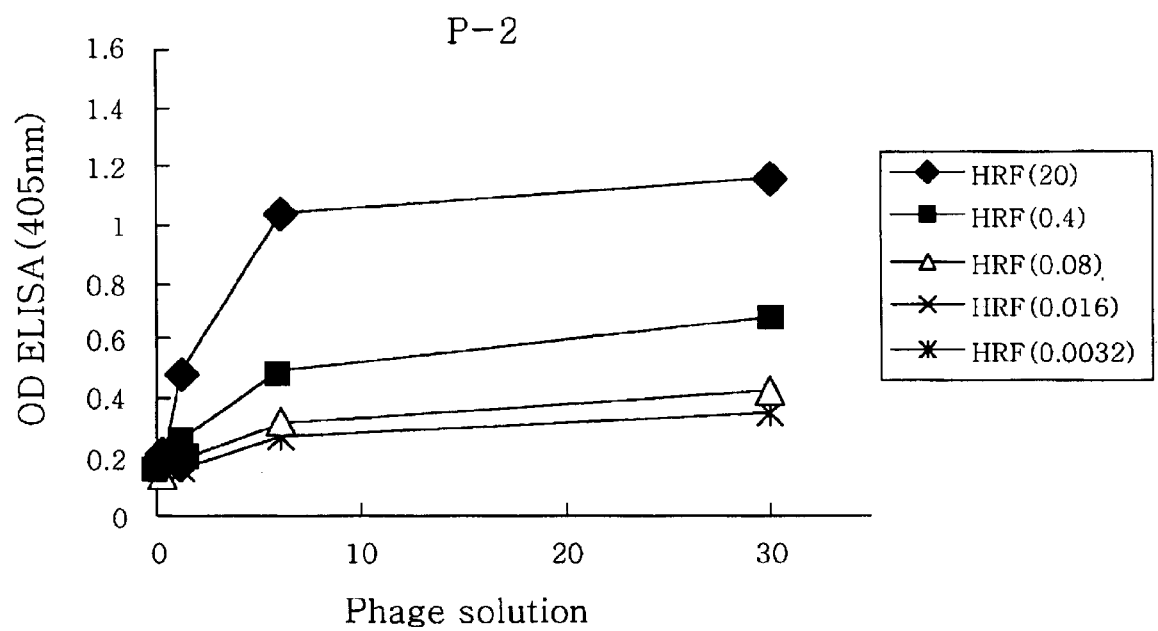
FIG. 13 is a graph showing the binding affinity of peptides encoded by the phages with HRF.

HRF was 1/5-fold serially diluted from 20 μg/ml (20, 4, 0.8, 0.16, 0.032 μg/ml, respectively) and immobilized in a plastic well at a volume of 50 μl. Thereto was added 1/5-fold serially diluted phage ph2 solution (½, 1/10, 1/50, 1/250 and 1/1250 of the original solution). ELISA was carried out and the chromogenicity was measured at 405 nm. The results are shown in FIG. 13. From FIG. 13, it can be seen that ph2 clone retained the specific binding affinity with HRF even at the diluted concentrations of 0.4, 0.08, 0.016 and 0.032 μg/ml.

EXAMPLE 13

Figure 14A:
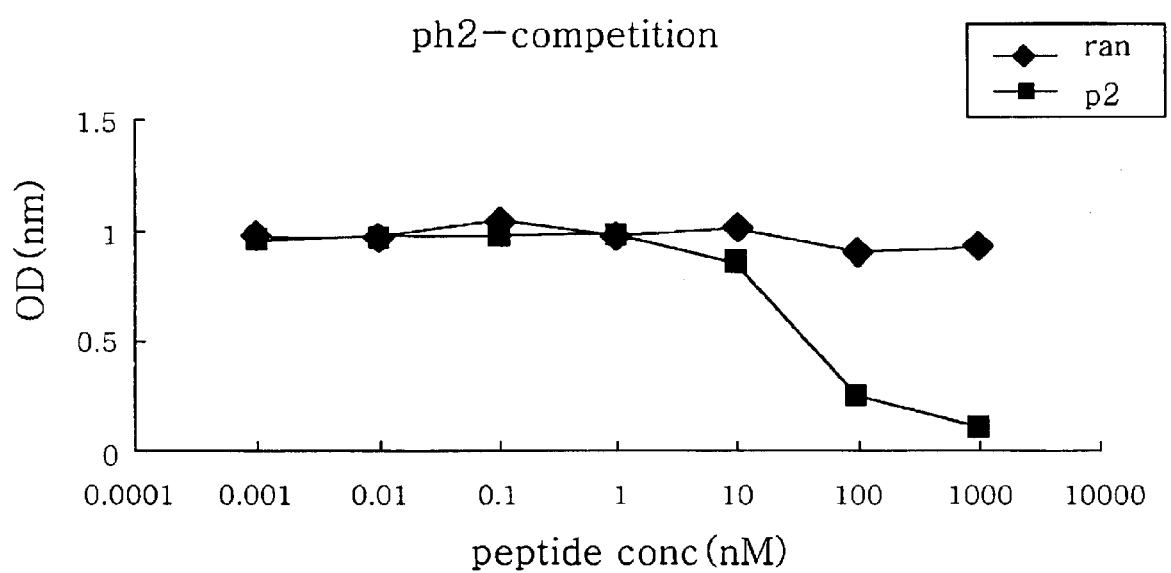
FIGS. 14a to 14c are graphs showing the competition of HRF-binding phage-displayed peptides and synthetic peptides having the identical amino acid sequence therewith.
Figure 14B:
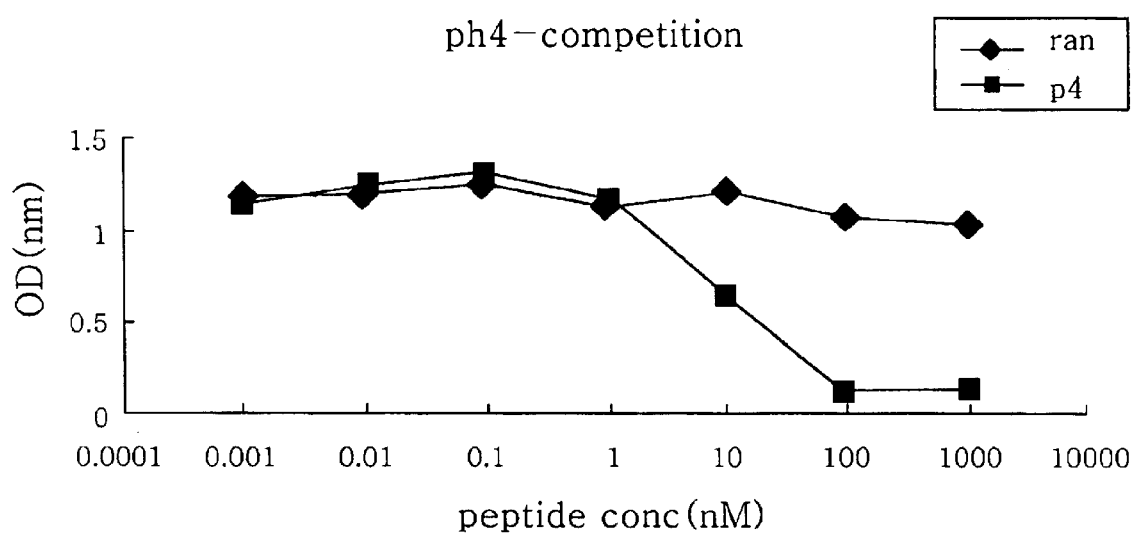
Figure 14C:
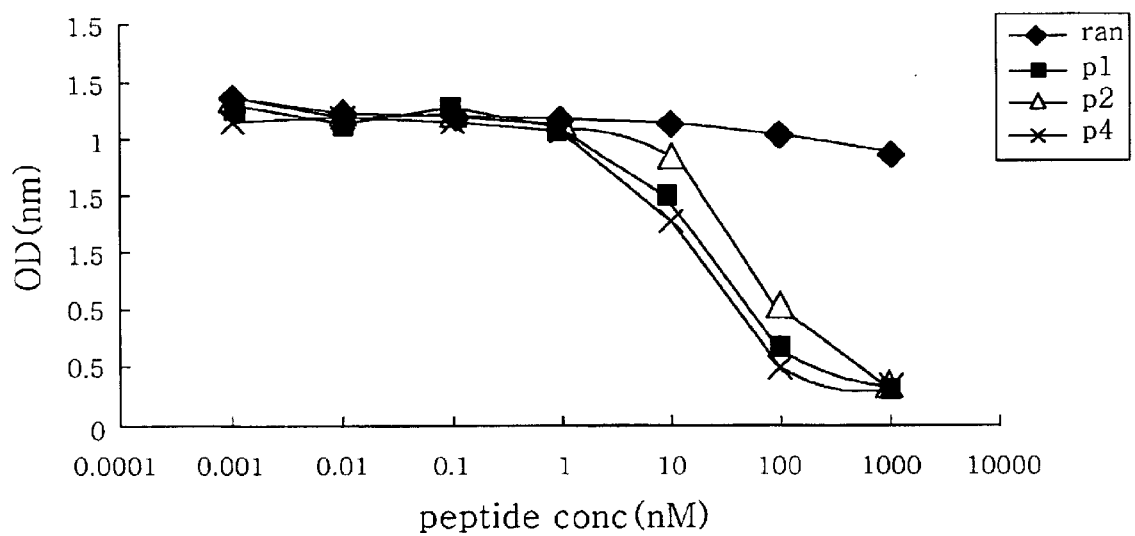

Competition Binding Assay a) Only the phage clones having the specific affinity in ELISA (ph2 and ph4) were sequenced to identify the displayed peptide sequences and then, hetapeptides (p2 and p4) was synthesized. Also, as a negative control, random peptide (ran, amino acid sequence: LMEGCRA) was synthesized. To the wells coated with HRF was added each 30 μl of the peptide solution serially diluted in 6% BSA/PBS from 1000 nM (1000, 100, 10, 1, 0.1, 0.01, 0.001 nM) and the solution was allowed to stand at room temperature for 30 minutes. The 1/25-fold diluted phage solution was added thereto and the whole solution was further allowed to stand for 2 hours. The solution was washed five times with PBST and then, each 100 μl of HRP-conjugated anti-M13 antibodies were added thereto and then, the resulting mixture was allowed to stand for 1 hour. The mixture was washed 6 times with PBST and once with PBS, and thereto was added each 100 μl of peroxydase substrate solution to examine the competition. The results are shown in FIGS. 14a and 14b. It can be seen from the above figures that both of the synthetic peptides p2 and p4 bind to HRF competitively with phage clones ph2 and ph4.

b) In order to test whether or not p1, p2 and p4 bind to the identical site on HRF, the wells were coated with HRF according to the substantially same procedure as in the above a). Competitive binding analysis of p1, p2 and p4 on ph2 was carried out, whose results are shown in FIG. 14c. As shown FIG. 14c, p1, p2 and p4 bound to the identical site on HRF.

EXAMPLE 14

Amino Acid Sequence Variations in HRF Binding Peptides

In order to identify the residues involving in the HRF binding affinity of the heptapeptides of the present invention, each amino acid in p2 was substituted with alanine (A), provided that an amino acid was substituted with Lysine (K) in m5 (see Table 2).

TABLE 2

| Heptapeptide | Amino acid sequence |
|---|---|
| p2 | WYVYPSM |
| m1 | AYVYPSM |
| m2 | WAVYPSM |
| m3 | WYAYPSM |
| m4 | WYVAPSM |
| m5 | WYVYKSM |
| m6 | WYVYPAM |
| m7 | WYVYPSA |

Figure 15:
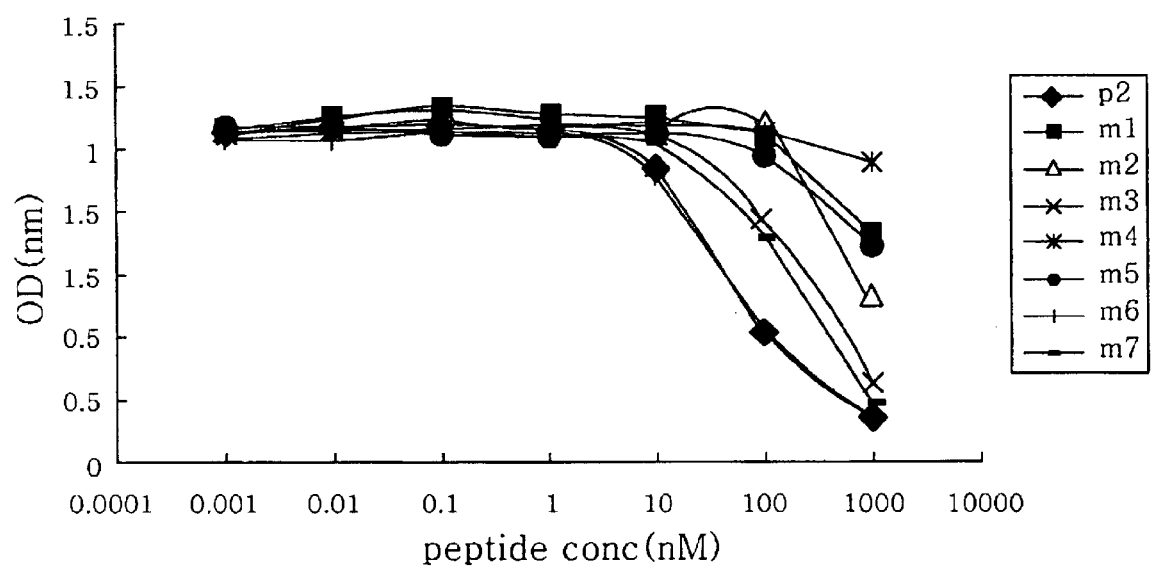
FIG. 15 is a graph comparing the HRF binding affinities of the peptides in accordance with the present invention.

The HRF binding affinity of the above peptides was measured according to the substantially same procedure as in Example 11. The results are shown in FIG. 15 and as shown in FIG. 15, the HRF binding affinity was p2, m6>m7>m3>m2>m5>m1>m4.

EXAMPLE 15

Measurement of Histamine Release

Figure 16:
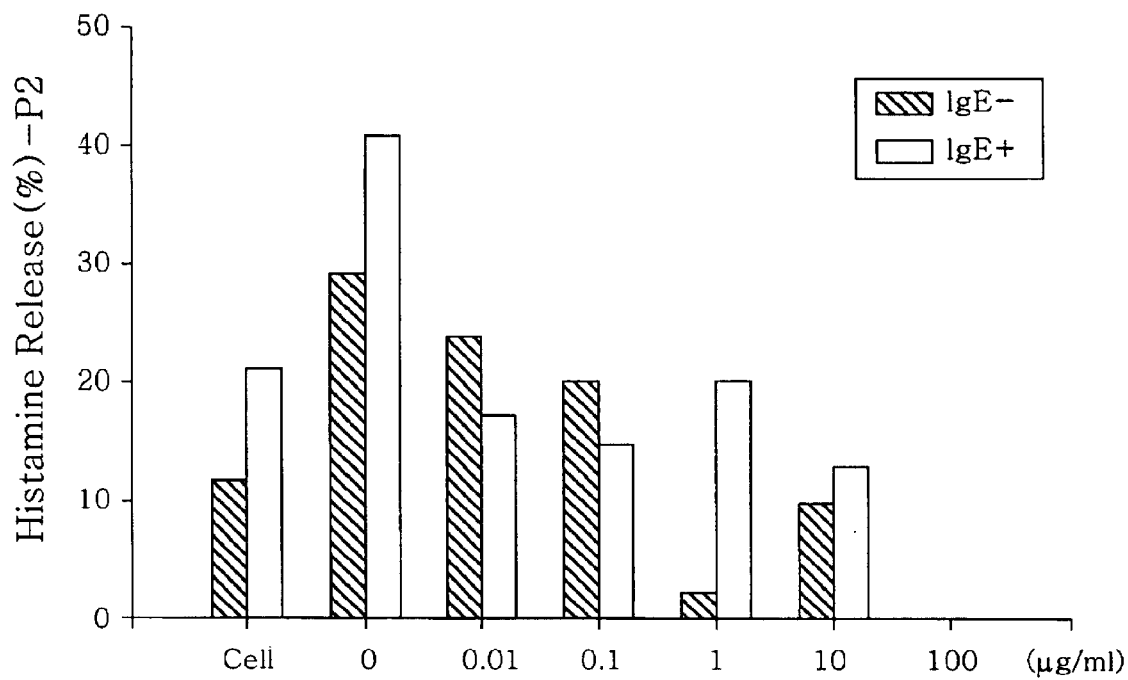
FIG. 16 is a graph showing the dose-response results to measure an amount required for inhibition of histamine release by the HRF-binding peptides in RBL-2H3 cell line.
Figure 17:
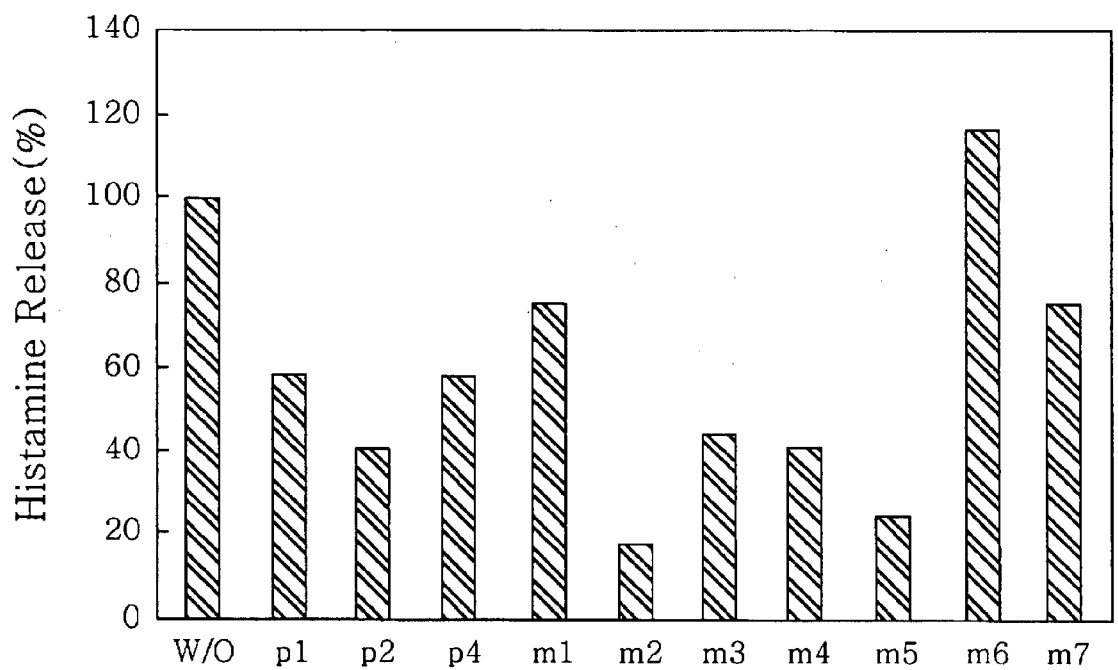
FIG. 17 is a graph comparing the inhibition of histamine release by HRF of the HRF-binding peptides in RBL-2H3 cell line.
Figure 22:
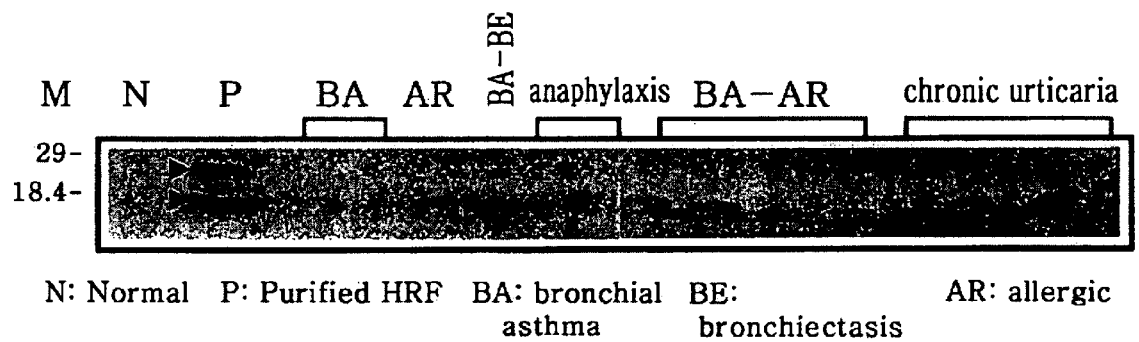
FIG. 22 shows the HRF detection in various allergy patients.

The full-length rat HRF sequence (Chitpatima, et al., 1988) amplified by PCR was cloned in pRSET-A vector and overexpressed in E. coli. The expressed recombinant protein was purified by His-bound Ni column (Novagen) and used for the stimulation of RBL-2H3 cells. RBL-2H3 cells were grown in 24-well plate at 1×10$^6$ cells, sensitized with rat IgE antibodies (0.2 μg/ml, Serotec) for 45~60 minutes and then, treated with 20 μg/ml of the recombinant HRF protein (positive control). The cells as prepared above were dose-dependently treated with heptamer peptides p1 and p2. Also, they were treated with the recombinant HRF protein and peptides p1, p2, p4 and m1 to m7 at the same concentration as that of HRF, i.e. 20 μg/ml, respectively, The obtained sample was prepared to acylated histamine using RIA-analysis kit (Immunotech, France) and then, competitively bound to $^{125}$I-acylated histamine and monoclonal antibodies. This sample was reanalyzed in γ-counter. The results are shown in FIGS. 16 and 17. As shown in FIG. 16, in RBL-2H3 cells, 0.01 μg/ml or more of the peptide of SEQ ID No. 14 (p2) inhibited histamine release, and as shown in FIG. 17, at a concentration of 20 μg/ml, p1, p2, p4, m1 to m5 and m7 inhibited histamine release by HRF (m2>m5>m4>p2>m3>p1=p4>m1>m7). However, m6 conversely stimulated histamine release.

EXAMPLE 16

Analysis of Effects on Neurotransmitters Release by HRF

It was examined whether or not HRF functions as the inhibitor of (Na,K)ATPase enzyme to stimulate neurotransmitters release. For this purpose, HRF was added to the culture solution of PC12 cells (Abu-Raya, et al., 1999) and then, changes in [$^3$H]-labeled dopamine release induced in basal and K$^+$-depolarized state by addition of HRF were measured. PC12 cells from passage numbers 5 to 15 were cultured in RPMI-1640 medium containing 10% horse serum, 5% fetal bovine serum, penicillin (100 U/ml) and streptomycin (100 µg/ml) with the supply of 5% $CO_2$ at 37° C.

To measure [$^3$H]-dopamine release, one day prior to the experiment, the cells (1×10$^{-6}$ cells/well) were cultured in 12-well dish coated with poly-L-lysine (10 µg/ml). The fresh medium containing [$^3$H]-dopamine (0.5 µCi/ml) was loaded thereto and then, the cells were further cultured at 37° C. for 3 hours. They were washed 2 or 3 times with 1 ml of PBS(1×) per well. To Krebs Ringer (KR) buffer (125 mM NaCl, 5 mM KCl, 2 mM $CaCl_2$, 10 mM HEPES, 1.2 mM $MgSO_4$, 1.2 mM $KH_2PO_4$, 6 mM glucose, 5 mM $NaHCO_3$), ascorbic acid (0.2 mg/ml), pargyline (0.6 mg/ml) and desipramine (2 µM) were added. Each 1 ml of the mixture was loaded with HRF and the reaction was proceeded at 37° C. for 20 minutes. The release in the depolarization state was measured in KR buffer containing 50 mM KCl, and in $Ca^{2+}$-free medium, was measured in KR buffer prepared by removal of $CaCl_2$ with the addition of 0.5 mM EGTA.

Upon completion of the reaction, the radioactivity of the released dopamine was measured after centrifuging the culture solution at 4° C., 1,000×g for 10 minutes. The cells were solubilized with 0.5 N NaOH and then, the radioactivity within the tissue was measured. The release rate (%) of dopamine was calculated by [radioactivity of the supernatant/(radioactivity of the supernatant+radioactivity within the tissue)×100].

Figure 23:
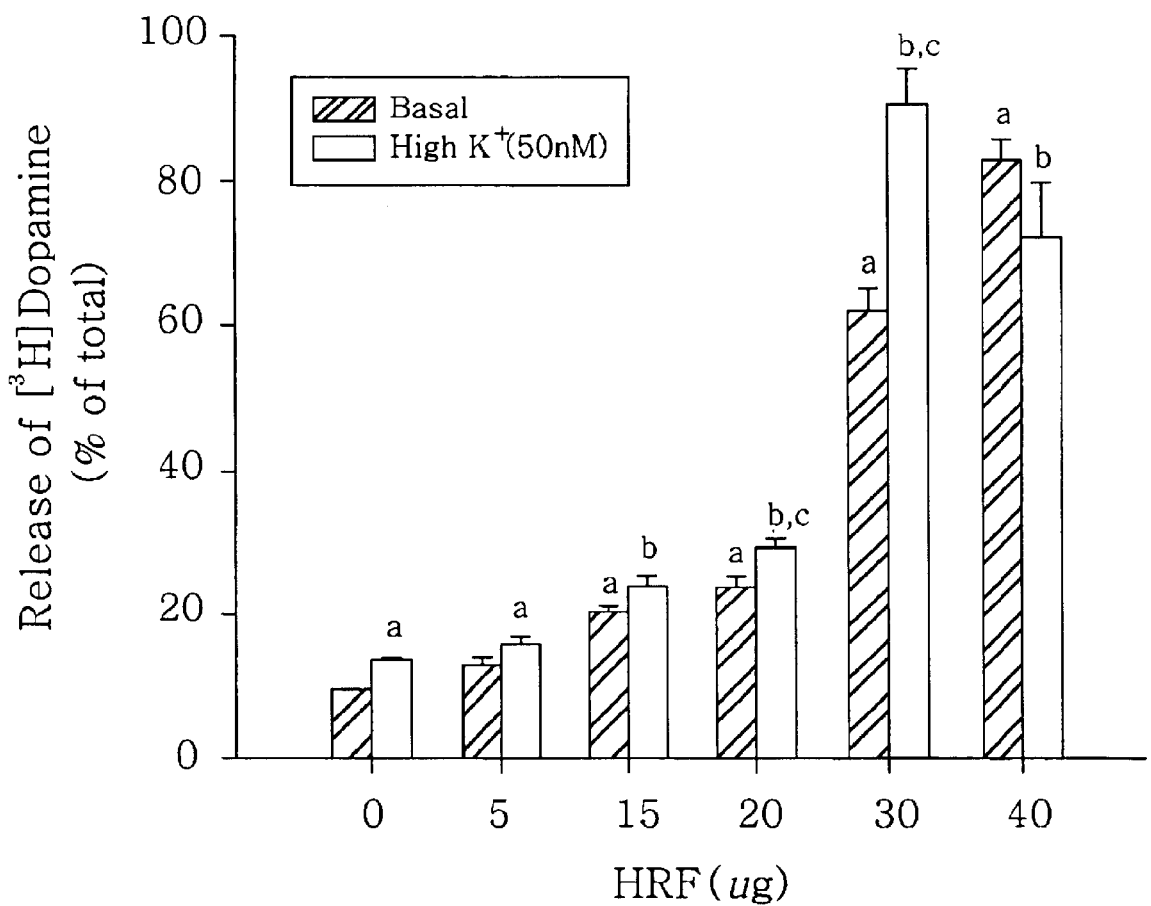
FIG. 23 is a graph showing the dose-dependent increase in dopamine release by HRF in PC12 cells; and, FIG. 24 is a graph showing the inhibition of dopamine release induced by HRF by the HRF-binding peptides in PC12 cells.

The results are shown in FIG. 23. As shown in FIG. 23, HRF dose-dependently increased the basal release of dopamine in nerve cell-like PC12 cells. That is, in case of treatment of HRF at a concentration of 10 µg, dopamine release was increased to the extent similar to the K$^+$-stimulated release in depolarization. In case of treatment of HRF at a concentration of 30 µg or more, dopamine release was steeply increased and from this time, the cells were not adhered to the surface of culture dish any longer and finally, reached to death. HRF also dose-dependently increased K$^+$-stimulated dopamine release in depolarization. As compared with the increase in basal release, the increase in K$^+$-stimulated release was shifted to left, but the extent thereof was relatively small.

EXAMPLE 17

Measurement of Inhibitory Activity of HRF-binding Peptides on Neurotransmitters Release by HRF In order to confirm whether the peptides blocking histamine release by HRF also block neurotransmitters release in nerve cells, the peptide of SEQ ID No. 14 (p2) was tested for its effects on dopamine release stimulated by HRF according to the substantially same procedure as in Example 16.

Figure 24:
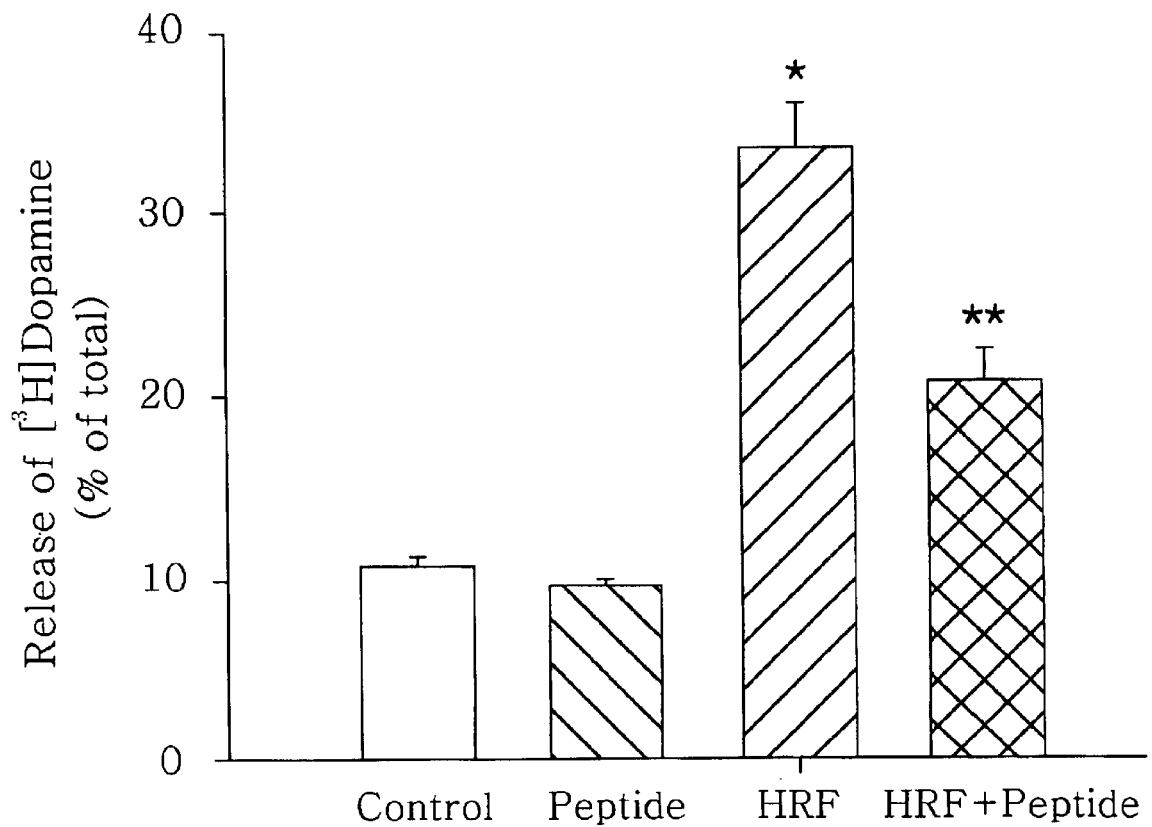

The results are shown in FIG. 24. As shown in FIG. 24, dopamine release about 110% increased by 15 µg/ml of HRF was about 60% inhibited by 60 µg/ml of p2. Consequently, the HRF-binding peptide also effectively blocked neurotransmitters release increased by HRF in nerve cells.

Industrial Applicability

The present inventors first revealed the identity of HRF receptor and stimulation mechanism of histamine release by HRF in basophils. Accordingly, the intracellular histamine release can be effectively inhibited by using HRF-binding peptides having the similar reaction mechanism to HRF receptor, of good pharmacokinetic properties and high stability. Therefore, the HRF-binding peptides can be used in the diagnosis, prophylaxis and treatment of allergies such as such as asthma, rhinitis, urticaria, anaphylaxis, allergic bronchiectasis, allergies due to foods, drugs, pollen, insects, etc., hay fever, cold urticaria, or atopic dermatitis, in human or animals.

Further, BRF involving in the regulation of intracellular (Na,K)ATPase activity stimulates neurotransmitters release by inhibition of (Na,K)-ATPase playing an important role in neuroactivity in nerve cells and thus, plays an important role in pathophysiological effects in nerve cells and brain. Therefore, the peptides blocking the increase in neurotransmitters release by HRF are useful in the diagnosis, prophylaxis or treatment of various apoptosis-associated diseases such as cerebral apoplexy, Alzheimer's disease or Parkinson's disease.

Still further, HRF receptor or HRF-binding peptides can be used in the diagnosis, prophylaxis or treatment of malaria.

Various non-peptide agents can be also prepared by using HRF receptor or HRF-binding peptides as precursors.

What is claimed is:

1. An isolated histamine releasing factor (HRF) binding peptide having the amino acid sequence as represented by the following formula:

(A, L or W)-(V, Y, E or A)-(T, V, F or A)-(Y, P or A)-(P, G or K)-(A, L, S or W)-(A, P or M).

2. The peptide according to claim 1, which has the amino acid sequence selected from the group consisting of SEQ ID NOS: 13, 14, 15, 16, 17, 18, 19, 20, 21 and 22.

3. The peptide according to claim 1, which has the amino acid sequence (A or W)-(Y or A)-(V or A)-(Y or A)-(P or K)-(S or A)-(M or A).

4. The peptide according to claim 3, which has the amino acid sequence selected from the group consisting of SEQ ID NOS: 14, 16, 17, 18, 19, 20, 21 and 22.

5. The peptide according to claim 3, which has the amino acid sequence W-(Y or A)-(V or A)-(Y or A)-(P or K)-(S or A)-M.

6. The peptide according to claim 5, which has the amino acid sequence selected from the group consisting of SEQ ID NOS: 14, 17, 18, 19, 20 and 21.

7. A composition for diagnosis, prophylaxis or treatment of allergies, comprising as an active ingredient the peptide according to any one of claims 1 to 6.

8. The composition according to claim 7, wherein the allergy is asthma, rhinitis, urticaria, anaphylaxis, allergic bronchiectasis, allergies due to foods, drugs, pollen, insects, hay fever, cold urticaria, or atopic dermatitis.

9. An agent for inhibiting histamine or dopamine release, comprising as an active ingredient the peptide according to any one of claims 1 to 6.

10. A method of inhibiting histamine release comprising administering to an individual in need thereof a compound according to claim 1.

* * * * *

SEQUENCE LISTING

```
<160> NUMBER OF SEQ ID NOS: 22

<210> SEQ ID NO 1
<211> LENGTH: 446
<212> TYPE: PRT
<213> ORGANISM: Rattus sp.

<400> SEQUENCE: 1

Val Ala Asn Val Pro Glu Val Leu Leu Ala Thr Val Thr Val Cys Leu
 1               5                  10                  15

Thr Leu Thr Ala Lys Arg Met ala Arg Lys Asn Cys Leu Val Lys Asn
            20                  25                  30

Leu Glu Ala Val Glu Thr Leu Gly Ser Thr Ser Thr Ile Cys Ser Asp
        35                  40                  45
```

-continued

```
Lys Thr Gly Thr Leu Thr Gln Asn Arg Met Thr Val Ala His Met Trp
 50                  55                  60

Phe Asp Asn Gln Ile His Glu Ala Asp Thr Thr Glu Asn Gln Ser Gly
 65                  70                  75                  80

Val Ser Phe Asp Lys Thr Ser Ala Thr Trp Phe Ala Leu Ser Arg Ile
                 85                  90                  95

Ala Gly Leu Cys Asn Arg Ala Val Phe Gln Ala Asn Gln Glu Asn Leu
                100                 105                 110

Pro Ile Leu Lys Arg Ala Val Ala Gly Asp Ala Ser Glu Ser Ala Leu
                115                 120                 125

Leu Lys Cys Ile Glu Val Cys Cys Gly Ser Val Met Glu Met Arg Glu
            130                 135                 140

Lys Tyr Thr Lys Ile Val Glu Ile Pro Phe Asn Ser Thr Asn Lys Tyr
145                 150                 155                 160

Gln Leu Ser Ile His Lys Asn Pro Asn Ala Ser Glu Pro Lys His Leu
                165                 170                 175

Leu Val Met Lys Gly Ala Pro Glu Arg Ile Leu Asp Arg Cys Ser Ser
            180                 185                 190

Ile Leu Leu His Gly Lys Glu Gln Pro Leu Asp Glu Leu Lys Asp
            195                 200                 205

Ala Phe Gln Asn Ala Tyr Leu Glu Leu Gly Gly Leu Gly Glu Arg Val
210                 215                 220

Leu Gly Phe Cys His Leu Leu Pro Asp Glu Gln Phe Pro Glu Gly
225                 230                 235                 240

Phe Gln Phe Asp Thr Asp Glu Val Asn Phe Pro Val Asp Asn Leu Cys
                245                 250                 255

Phe Val Gly Leu Ile Ser Met Ile Asp Pro Pro Arg Ala Ala Val Pro
                260                 265                 270

Asp Ala Val Gly Lys Cys Arg Ser Ala Gly Ile Lys Val Ile Met Val
                275                 280                 285

Thr Gly Asp His Pro Ile Thr Ala Lys Ala Ile Ala Lys Gly Val Gly
            290                 295                 300

Ile Ile Ser Glu Gly Asn Glu Thr Val Glu Asp Ile Ala Ala Arg Leu
305                 310                 315                 320

Asn Ile Pro Val Asn Gln Val Asn Pro Arg Asp Ala Lys Ala Cys Val
                325                 330                 335

Val His Gly Ser Asp Leu Lys Asp Met Thr Ser Glu Glu Leu Asp Asp
                340                 345                 350

Ile Leu Arg Tyr His Thr Glu Ile Val Phe Ala Arg Thr Ser Pro Gln
            355                 360                 365

Gln Lys Leu Ile Ile Val Glu Gly Cys Gln Arg Gln Gly Ala Ile Val
            370                 375                 380

Ala Val Thr Gly Asp Gly Val Asn Asp Ser Pro Ala Leu Lys Lys Ala
385                 390                 395                 400

Asp Ile Gly Val Ala Met Gly Ile Val Gly Ser Asp Val Ser Lys Gln
                405                 410                 415

Ala Ala Asp Met Ile Leu Leu Asp Asp Asn Phe Ala Ser Ile Val Thr
                420                 425                 430

Gly Val Glu Glu Gly Arg Leu Ile Phe Asp Asn Leu Lys Lys
            435                 440                 445

<210> SEQ ID NO 2
<211> LENGTH: 446
```

-continued

```
<212> TYPE: PRT
<213> ORGANISM: Rattus sp.
<220> FEATURE:
<221> NAME/KEY: UNSURE
<222> LOCATION: (1)..(446)
<223> OTHER INFORMATION: Xaa = any amino acid, unknown or other

<400> SEQUENCE: 2
```

| | | | | | | | | | | | | | | | |
|---|---|---|---|---|---|---|---|---|---|---|---|---|---|---|---|
| Val | Ala | Asn | Val | Pro | Glu | Gly | Leu | Leu | Ala | Thr | Val | Thr | Val | Cys | Leu |
| 1 | | | | 5 | | | | | 10 | | | | | 15 | |
| Thr | Leu | Thr | Ala | Lys | Arg | Met | ala | Arg | Lys | Asn | Cys | Leu | Val | Lys | Asn |
| | | | | 20 | | | | | 25 | | | | | 30 | |
| Leu | Glu | Ala | Val | Glu | Thr | Leu | Gly | Ser | Thr | Ser | Thr | Ile | Cys | Ser | Asp |
| | | | | 35 | | | | | 40 | | | | | 45 | |
| Lys | Thr | Gly | Thr | Leu | Thr | Gln | Asn | Arg | Met | Thr | Val | Ala | His | Met | Trp |
| | | | | 50 | | | | | 55 | | | | | 60 | |
| Phe | Asp | Asn | Gln | Ile | His | Glu | Ala | Asp | Thr | Thr | Glu | Asp | Gln | Ser | Gly |
| 65 | | | | | 70 | | | | | 75 | | | | | 80 |
| Ala | Thr | Phe | Asp | Lys | Arg | Ser | Pro | Thr | Trp | Thr | Ala | Leu | Ser | Arg | Ile |
| | | | | 85 | | | | | 90 | | | | | 95 | |
| Ala | Gly | Leu | Cys | Asn | Arg | Ala | Val | Phe | Lys | Ala | Gly | Gln | Glu | Asn | Ile |
| | | | | 100 | | | | | 105 | | | | | 110 | |
| Ser | Val | Ser | Lys | Arg | Asp | Thr | Ala | Gly | Asp | Ala | Ser | Glu | Ser | Ala | Leu |
| | | | | 115 | | | | | 120 | | | | | 125 | |
| Leu | Lys | Cys | Ile | Glu | Leu | Ser | Cys | Gly | Ser | Val | Arg | Lys | Met | Arg | Asp |
| | | | | 130 | | | | | 135 | | | | | 140 | |
| Arg | Asn | Pro | Lys | Val | Ala | Glu | Ile | Pro | Phe | Asn | Ser | Thr | Asn | Lys | Tyr |
| 145 | | | | | 150 | | | | | 155 | | | | | 160 |
| Gln | Leu | Ser | Ile | His | Glu | Arg | Glu | Asp | Xaa | Ser | Pro | Gln | Ser | His | Val |
| | | | | 165 | | | | | 170 | | | | | 175 | |
| Leu | Val | Met | Lys | Gly | Ala | Pro | Glu | Arg | Ile | Leu | Asp | Arg | Cys | Ser | Thr |
| | | | | 180 | | | | | 185 | | | | | 190 | |
| Ile | Leu | Val | Gln | Gly | Lys | Glu | Ile | Pro | Leu | Asp | Lys | Glu | Met | Gln | Asp |
| | | | | 195 | | | | | 200 | | | | | 205 | |
| Ala | Phe | Gln | Asn | Ala | Tyr | Met | Glu | Leu | Gly | Gly | Leu | Gly | Glu | Arg | Val |
| | | | | 210 | | | | | 215 | | | | | 220 | |
| Leu | Gly | Phe | Cys | Gln | Leu | Asn | Leu | Pro | Ser | Gly | Lys | Phe | Pro | Arg | Gly |
| 225 | | | | | 230 | | | | | 235 | | | | | 240 |
| Phe | Lys | Phe | Asp | Thr | Asp | Glu | Leu | Asn | Phe | Pro | Thr | Glu | Lys | Leu | Cys |
| | | | | 245 | | | | | 250 | | | | | 255 | |
| Phe | Val | Gly | Leu | Met | Ser | Met | Ile | Asp | Pro | Pro | Arg | Ala | Ala | Val | Pro |
| | | | | 260 | | | | | 265 | | | | | 270 | |
| Asp | Ala | Val | Gly | Lys | Cys | Arg | Ser | Ala | Gly | Ile | Lys | Val | Ile | Met | Val |
| | | | | 275 | | | | | 280 | | | | | 285 | |
| Thr | Gly | Asp | His | Pro | Ile | Thr | Ala | Lys | Ala | Ile | Ala | Lys | Gly | Val | Gly |
| | | | | 290 | | | | | 295 | | | | | 300 | |
| Ile | Ile | Ser | Glu | Gly | Asn | Glu | Thr | Val | Glu | Asp | Ile | Ala | Ala | Arg | Leu |
| 305 | | | | | 310 | | | | | 315 | | | | | 320 |
| Asn | Ile | Pro | Val | Ser | Gln | Val | Asn | Pro | Arg | Glu | Ala | Lys | Ala | Cys | Val |
| | | | | 325 | | | | | 330 | | | | | 335 | |
| Val | His | Gly | Ser | Asp | Leu | Lys | Asp | Met | Thr | Ser | Glu | Gln | Leu | Asp | Glu |
| | | | | 340 | | | | | 345 | | | | | 350 | |
| Ile | Leu | Arg | Asp | His | Thr | Glu | Ile | Val | Phe | Ala | Arg | Thr | Ser | Pro | Gln |
| | | | | 355 | | | | | 360 | | | | | 365 | |
| Gln | Lys | Leu | Ile | Ile | Val | Glu | Gly | Cys | Gln | Arg | Gln | Gly | Ala | Ile | Val |

```
            370                 375                 380
Ala Val Thr Gly Asp Gly Val Asn Asp Ser Pro Ala Leu Lys Lys Ala
385                 390                 395                 400

Asp Ile Gly Ile Ala Met Gly Ile Ser Gly Ser Asp Val Ser Lys Gln
                405                 410                 415

Ala Ala Asp Met Ile Leu Leu Asp Asn Phe Ala Ser Ile Val Thr
                420                 425                 430

Gly Val Glu Glu Gly Arg Leu Ile Phe Asp Asn Leu Lys Lys
            435                 440                 445

<210> SEQ ID NO 3
<211> LENGTH: 446
<212> TYPE: PRT
<213> ORGANISM: Rattus sp.

<400> SEQUENCE: 3

Val Ala Asn Val Pro Glu Gly Leu Leu Ala Thr Val Thr Val Cys Leu
 1               5                  10                  15

Thr Leu Thr Ala Lys Arg Met ala Arg Lys Asn Cys Leu Val Lys Asn
                20                  25                  30

Leu Glu Ala Val Glu Thr Leu Gly Ser Thr Ser Thr Ile Cys Ser Asp
            35                  40                  45

Lys Thr Gly Thr Leu Thr Gln Asn Arg Met Thr Val Ala His Met Trp
     50                  55                  60

Phe Asp Asn Gln Ile His Glu Ala Asp Thr Thr Glu Asp Gln Ser Gly
 65                  70                  75                  80

Thr Ser Phe Asp Lys Ser Ser His Thr Trp Val Ala Leu Ser His Ile
                85                  90                  95

Ala Gly Leu Cys Asn Arg Ala Val Phe Lys Gly Gly Gln Asp Asn Ile
                100                 105                 110

Pro Val Leu Lys Arg Asp Val Ala Gly Asp Ala Ser Glu Ser Ala Leu
            115                 120                 125

Leu Lys Cys Ile Glu Leu Ser Ser Gly Ser Val Lys Leu Met Arg Glu
        130                 135                 140

Arg Asn Lys Lys Val Ala Glu Ile Pro Phe Asn Ser Thr Asn Lys Tyr
145                 150                 155                 160

Gln Leu Ser Ile His Glu Thr Glu Asp Pro Asn Asp Asn Arg Tyr Leu
                165                 170                 175

Leu Val Met Lys Gly Ala Pro Glu Arg Ile Leu Asp Arg Cys Ala Thr
            180                 185                 190

Ile Leu Leu Gln Gly Lys Glu Gln Pro Leu Asp Glu Glu Met Lys Glu
        195                 200                 205

Ala Phe Gln Asn Ala Tyr Leu Glu Leu Gly Gly Leu Gly Glu Arg Val
    210                 215                 220

Leu Gly Phe Cys His Tyr Tyr Leu Pro Glu Glu Gln Phe Pro Lys Gly
225                 230                 235                 240

Phe Ala Phe Asp Cys Asp Asp Val Asn Phe Thr Thr Asp Asn Leu Cys
                245                 250                 255

Phe Val Gly Leu Met Ser Met Ile Asp Pro Pro Arg Ala Ala Val Pro
            260                 265                 270

Asp Ala Val Gly Lys Cys Arg Ser Ala Gly Ile Lys Val Ile Met Val
        275                 280                 285

Thr Gly Asp His Pro Ile Thr Ala Lys Ala Ile Ala Lys Gly Val Gly
    290                 295                 300
```

```
Ile Ile Ser Glu Gly Asn Glu Thr Val Glu Asp Ile Ala Ala Arg Leu
305                 310                 315                 320

Asn Ile Pro Val Ser Gln Val Asn Pro Arg Asp Ala Lys Ala Cys Val
                325                 330                 335

Ile His Gly Thr Asp Leu Lys Asp Phe Thr Ser Glu Gln Ile Asp Glu
            340                 345                 350

Ile Leu Gln Asn His Thr Glu Ile Val Phe Ala Arg Thr Ser Pro Gln
            355                 360                 365

Gln Lys Leu Ile Ile Val Glu Gly Cys Gln Arg Gln Gly Ala Ile Val
370                 375                 380

Ala Val Thr Gly Asp Gly Val Asn Asp Ser Pro Ala Leu Lys Lys Ala
385                 390                 395                 400

Asp Ile Gly Val Ala Met Gly Ile Ala Gly Ser Asp Val Ser Lys Gln
                405                 410                 415

Ala Ala Asp Met Ile Leu Leu Asp Asn Phe Ala Ser Ile Val Thr
                420                 425                 430

Gly Val Glu Glu Gly Arg Leu Ile Phe Asp Asn Leu Lys Lys
            435                 440                 445

<210> SEQ ID NO 4
<211> LENGTH: 446
<212> TYPE: PRT
<213> ORGANISM: Homo sapiens

<400> SEQUENCE: 4

Val Ala Asn Val Pro Glu Gly Leu Leu Ala Thr Val Thr Val Cys Leu
  1               5                  10                  15

Thr Leu Thr Ala Lys Arg Met ala Arg Lys Asn Cys Leu Val Lys Asn
                20                  25                  30

Leu Glu Ala Val Glu Thr Leu Gly Ser Thr Ser Thr Ile Cys Ser Asp
            35                  40                  45

Lys Thr Gly Thr Leu Thr Gln Asn Arg Met Thr Val Ala His Met Trp
 50                  55                  60

Phe Asp Asn Gln Ile His Glu Ala Asp Thr Thr Glu Asn Gln Ser Gly
 65                  70                  75                  80

Val Ser Phe Asp Lys Thr Ser Ala Thr Trp Leu Ala Leu Ser Arg Ile
                85                  90                  95

Ala Gly Leu Cys Asn Arg Ala Val Phe Gln Ala Asn Gln Glu Asn Leu
            100                 105                 110

Pro Ile Leu Lys Arg Ala Val Ala Gly Asp Ala Ser Glu Ser Ala Leu
            115                 120                 125

Leu Lys Cys Ile Glu Leu Cys Cys Gly Ser Val Lys Glu Met Arg Glu
130                 135                 140

Arg Tyr Ala Lys Ile Val Glu Ile Pro Phe Asn Ser Thr Asn Lys Tyr
145                 150                 155                 160

Gln Leu Ser Ile His Lys Asn Pro Asn Thr Ser Glu Pro Gln His Leu
                165                 170                 175

Leu Val Met Lys Gly Ala Pro Glu Arg Ile Leu Asp Arg Cys Ser Ser
            180                 185                 190

Ile Leu Leu His Gly Lys Glu Gln Pro Leu Asp Glu Glu Leu Lys Asp
            195                 200                 205

Ala Phe Gln Asn Ala Tyr Leu Glu Leu Gly Gly Leu Gly Glu Arg Val
            210                 215                 220

Leu Gly Phe Cys His Leu Phe Leu Pro Asp Glu Gln Phe Pro Glu Gly
225                 230                 235                 240
```

```
Phe Gln Phe Asp Thr Asp Asp Val Asn Phe Pro Ile Asp Asn Leu Cys
                245                 250                 255

Phe Val Gly Leu Ile Ser Met Ile Asp Pro Pro Arg Ala Ala Val Pro
            260                 265                 270

Asp Ala Val Gly Lys Cys Arg Ser Ala Gly Ile Lys Val Ile Met Val
        275                 280                 285

Thr Gly Asp His Pro Ile Thr Ala Lys Ala Ile Ala Lys Gly Val Gly
    290                 295                 300

Ile Ile Ser Glu Gly Asn Glu Thr Val Glu Asp Ile Ala Ala Arg Leu
305                 310                 315                 320

Asn Ile Pro Val Ser Gln Val Asn Pro Arg Asp Ala Lys Ala Cys Val
                325                 330                 335

Val His Gly Ser Asp Leu Lys Asp Met Thr Ser Glu Gln Leu Asp Asp
            340                 345                 350

Ile Leu Lys Tyr His Thr Glu Ile Val Phe Ala Arg Thr Ser Pro Gln
        355                 360                 365

Gln Lys Leu Ile Ile Val Glu Gly Cys Gln Arg Gln Gly Ala Ile Val
    370                 375                 380

Ala Val Thr Gly Asp Gly Val Asn Asp Ser Pro Ala Leu Lys Lys Ala
385                 390                 395                 400

Asp Ile Gly Val Ala Met Gly Ile Ala Gly Ser Asp Val Ser Lys Gln
                405                 410                 415

Ala Ala Asp Met Ile Leu Leu Asp Asp Asn Phe Ala Ser Ile Val Thr
            420                 425                 430

Gly Val Glu Glu Gly Arg Leu Ile Phe Asp Asn Leu Lys Lys
        435                 440                 445

<210> SEQ ID NO 5
<211> LENGTH: 446
<212> TYPE: PRT
<213> ORGANISM: Homo sapiens
<220> FEATURE:
<221> NAME/KEY: UNSURE
<222> LOCATION: (1)..(446)
<223> OTHER INFORMATION: Xaa = any amino acid, unknown or other

<400> SEQUENCE: 5

Val Ala Asn Val Pro Glu Gly Leu Leu Ala Thr Val Thr Val Cys Leu
  1               5                  10                  15

Thr Leu Thr Ala Lys Arg Met ala Arg Lys Asn Cys Leu Val Lys Asn
            20                  25                  30

Leu Glu Ala Val Glu Thr Leu Gly Ser Thr Ser Thr Ile Cys Ser Asp
        35                  40                  45

Lys Thr Gly Thr Leu Thr Gln Asn Arg Met Thr Val Ala His Met Trp
    50                  55                  60

Phe Asp Asn Gln Ile His Glu Ala Asp Thr Thr Glu Asp Gln Ser Gly
65                  70                  75                  80

Ala Thr Phe Asp Lys Arg Ser Pro Thr Trp Thr Ala Leu Ser Arg Ile
                85                  90                  95

Ala Gly Leu Cys Asn Arg Ala Val Phe Lys Ala Gly Gln Glu Asn Ile
            100                 105                 110

Ser Val Ser Lys Arg Asp Thr Ala Gly Asp Ala Ser Glu Ser Ala Leu
        115                 120                 125

Leu Lys Cys Ile Glu Leu Ser Cys Gly Ser Val Arg Lys Met Arg Asp
    130                 135                 140
```

-continued

```
Arg Asn Pro Lys Val Ala Glu Ile Pro Phe Asn Ser Thr Asn Lys Tyr
145                 150                 155                 160

Gln Leu Ser Ile His Glu Arg Glu Asp Xaa Ser Pro Gln Ser His Val
            165                 170                 175

Leu Val Met Lys Gly Ala Pro Glu Arg Ile Leu Asp Arg Cys Ser Thr
        180                 185                 190

Ile Leu Val Gln Gly Lys Glu Ile Pro Leu Asp Lys Glu Met Gln Asp
    195                 200                 205

Ala Phe Gln Asn Ala Tyr Met Glu Leu Gly Leu Gly Glu Arg Val
210                 215                 220

Leu Gly Phe Cys Gln Leu Asn Leu Pro Ser Gly Lys Phe Pro Arg Gly
225                 230                 235                 240

Phe Lys Phe Asp Thr Asp Glu Leu Asn Phe Pro Thr Glu Lys Leu Cys
                245                 250                 255

Phe Val Gly Leu Met Ser Met Ile Asp Pro Pro Arg Ala Ala Val Pro
            260                 265                 270

Asp Ala Val Gly Lys Cys Arg Ser Ala Gly Ile Lys Val Ile Met Val
        275                 280                 285

Thr Gly Asp His Pro Ile Thr Ala Lys Ala Ile Ala Lys Gly Val Gly
    290                 295                 300

Ile Ile Ser Glu Gly Asn Glu Thr Val Glu Asp Ile Ala Ala Arg Leu
305                 310                 315                 320

Asn Ile Pro Met Ser Gln Val Asn Pro Arg Glu Ala Lys Ala Cys Val
                325                 330                 335

Val His Gly Ser Asp Leu Lys Asp Met Thr Ser Glu Gln Leu Asp Glu
            340                 345                 350

Ile Leu Lys Asn His Thr Glu Ile Val Phe Ala Arg Thr Ser Pro Gln
        355                 360                 365

Gln Lys Leu Ile Ile Val Glu Gly Cys Gln Arg Gln Gly Ala Ile Val
    370                 375                 380

Ala Val Thr Gly Asp Gly Val Asn Asp Ser Pro Ala Leu Lys Lys Ala
385                 390                 395                 400

Asp Ile Gly Ile Ala Met Gly Ile Ser Gly Ser Asp Val Ser Lys Gln
                405                 410                 415

Ala Ala Asp Met Ile Leu Leu Asp Asp Asn Phe Ala Ser Ile Val Thr
            420                 425                 430

Gly Val Glu Glu Gly Arg Leu Ile Phe Asp Asn Leu Lys Lys
        435                 440                 445

<210> SEQ ID NO 6
<211> LENGTH: 446
<212> TYPE: PRT
<213> ORGANISM: Homo sapiens

<400> SEQUENCE: 6

Val Ala Asn Val Pro Glu Gly Leu Leu Ala Thr Val Thr Val Cys Leu
1               5                   10                  15

Thr Val Thr Ala Lys Arg Met ala Arg Lys Asn Cys Leu Val Lys Asn
            20                  25                  30

Leu Glu Ala Val Glu Thr Leu Gly Ser Thr Ser Thr Ile Cys Ser Asp
        35                  40                  45

Lys Thr Gly Thr Leu Thr Gln Asn Arg Met Thr Val Ala His Met Trp
    50                  55                  60

Phe Asp Asn Gln Ile His Glu Ala Asp Thr Thr Glu Asp Gln Ser Gly
65                  70                  75                  80
```

```
Thr Ser Phe Asp Lys Ser Ser His Thr Trp Val Ala Leu Ser His Ile
                85                  90                  95
Ala Gly Leu Cys Asn Arg Ala Val Phe Lys Gly Gly Gln Asp Asn Ile
            100                 105                 110
Pro Val Leu Lys Arg Asp Val Ala Gly Asp Ala Ser Glu Ser Ala Leu
        115                 120                 125
Leu Lys Cys Ile Glu Leu Ser Ser Gly Ser Val Lys Leu Met Arg Glu
    130                 135                 140
Arg Asn Lys Lys Val Ala Glu Ile Pro Phe Asn Ser Thr Asn Lys Tyr
145                 150                 155                 160
Gln Leu Ser Ile His Glu Thr Glu Asp Pro Asn Asp Asn Arg Tyr Leu
                165                 170                 175
Leu Val Met Lys Gly Ala Pro Glu Arg Ile Leu Asp Arg Cys Ser Thr
            180                 185                 190
Ile Leu Leu Gln Gly Lys Glu Gln Pro Leu Asp Glu Met Lys Glu
        195                 200                 205
Ala Phe Gln Asn Ala Tyr Leu Glu Leu Gly Gly Leu Gly Glu Arg Val
    210                 215                 220
Leu Gly Phe Cys His Tyr Tyr Leu Pro Glu Glu Gln Tyr Pro Gln Gly
225                 230                 235                 240
Phe Ala Phe Asp Cys Asp Asp Val Asn Phe Thr Thr Asp Asn Leu Cys
                245                 250                 255
Phe Val Pro Leu Met Ser Met Ile Gly Pro Pro Arg Ala Ala Val Pro
            260                 265                 270
Asp Ala Val Gly Lys Cys Arg Ser Ala Gly Ile Lys Val Ile Met Val
        275                 280                 285
Thr Gly Asp His Pro Ile Thr Ala Lys Ala Ile Ala Lys Gly Val Gly
    290                 295                 300
Ile Ile Ser Glu Gly Asn Glu Thr Val Glu Asp Ile Ala Ala Arg Leu
305                 310                 315                 320
Asn Ile Pro Val Ser Gln Val Asn Pro Arg Asp Ala Lys Ala Cys Val
                325                 330                 335
Ile His Gly Thr Asp Leu Lys Asp Phe Thr Ser Glu Gln Ile Asp Glu
            340                 345                 350
Ile Leu Gln Asn His Thr Glu Ile Val Phe Ala Arg Thr Ser Pro Gln
        355                 360                 365
Gln Lys Leu Ile Ile Val Glu Gly Cys Gln Arg Gln Gly Ala Ile Val
    370                 375                 380
Ala Val Thr Gly Asp Gly Val Asn Asp Ser Pro Ala Leu Lys Lys Ala
385                 390                 395                 400
Asp Ile Gly Val Ala Met Gly Ile Ala Gly Ser Asp Val Ser Lys Gln
                405                 410                 415
Ala Ala Asp Met Ile Leu Leu Asp Asp Asn Phe Ala Ser Ile Val Thr
            420                 425                 430
Gly Val Glu Glu Gly Arg Leu Ile Phe Asp Asn Leu Lys Lys
        435                 440                 445
```

<210> SEQ ID NO 7
<211> LENGTH: 1338
<212> TYPE: DNA
<213> ORGANISM: Rattus sp.

<400> SEQUENCE: 7
gtagccaacg tgccggaagt tttgctggcc accgtcacgg tatgtctgac gctcactgcc    60

```
aagcgcatgg ccaggaagaa ctgcctggtg aagaacctgg aagctgtgga gaccttgggg      120
tccacatcca ccatctgctc cgacaagact ggaactctga ctcagaaccg atgacagtg       180 gctcacatgt ggtttgacaa tcaaatccat gaagctgaca ccacagagaa tcagagtggg      240
gtctcctttg acaagacgtc agccacctgg ttcgctctgt ccagaattgc tggtctctgt      300
aacagggcag tgtttcaggc taaccaggaa acctgcctta cctgaagcg tgcagtagcg       360 ggagatgctt ccgagtcggc gctcctaaag tgcatcgagg tctgctgtgg ctccgtgatg      420
gagatgaggg agaagtacac caagatagtg agattccttt caactccac caacaagtac       480 cagctctcca ttcacaagaa cccaaacgca tcggagccta agcacctgct agtgatgaag      540
ggcgccccag aaaggatcct ggaccgatgc agttctatcc tcctccacgg caaggagcag      600
cccctggacg aagagctgaa ggacgccttt cagaatgcct acctggagct gggtggcctg      660
ggagaacgtg tgctaggttt ctgccacctc cttctgcctg acgaacagtt tcctgaaggc      720
ttccagtttg acactgatga agtcaatttc ccgtggata acctctgctt cgtgggtctt        780
atctccatga ttgaccctcc tcgagctgct gtccccgatg ctgtgggcaa atgccgcagc      840
gctgggatta aggtcatcat ggtcacagga gaccatccaa tcacagccaa agccattgct      900
aagggggtgg gcattatctc agaaggtaac gagaccgtgg aagacattgc tgcccgcctc      960
aacattccag tgaaccaggt gaaccccaga gatgccaagg cctgtgtagt acatggcagt      1020
gacttgaagg acatgacctc tgaggagctg atgacatttt gcggtaccac acggagatt       1080 gtctttgcta ggacctctcc tcaacagaag ctcatcattg tggagggctg ccagcggcag      1140
ggtgccatcg tggctgtcac aggggatggt gtcaatgact ctccagcttt gaaaaaggca      1200
gatattgggg ttgccatggg gattgttggc tcggatgtgt ccaagcaagc tgctgacatg      1260
attcttctgg atgacaactt tgcctccatc gtgactggag tagaagaagg tcgtctgata      1320
tttgataact tgaagaaa                                                     1338
```

<210> SEQ ID NO 8
<211> LENGTH: 1338
<212> TYPE: DNA
<213> ORGANISM: Rattus sp.
<220> FEATURE:
<221> NAME/KEY: UNSURE
<222> LOCATION: (1)..(1338)
<223> OTHER INFORMATION: n = a,c,g,t, any unknown or other

<400> SEQUENCE: 8

```
gtagccaacg tccccgaagg gctcttggcc actgttactg tgtgcctgac gctgacagcc       60
aagcgcatgg ctcgcaagaa ctgcctggtg aagaacctgg aggcggtgga gacgctgggc      120
tccacgtcca ccatctgctc ggacaagaca ggcaccctca cccagaaccg catgacggtg      180
gctcacatgt ggtttgacaa ccagatccat gaggctgaca ccactgaaga tcagtctggg      240
gccacttttg acaagcggtc cccgacgtgg acagccctgt ctcggatcgc tggtctctgc      300
aatcgtgccg tcttcaaggc tgggcaggag acatctccg tgtctaagcg ggacacagct       360
ggtgacgcct ctgagtcagc tctgctcaag tgcatcgagt tgtcctgtgg ctcagtgagg      420
aagatgaggg acaggaatcc aaggtggca gaaattccct tcaactctac caacaaatat       480
cagctttcca tccatgagag ggaagacagc ccccagagcc atgtgctgnn ngtgatgaaa      540
ggtgccccga gcgcatcct ggaccgatgc tctaccatcc tggtacaggg caaggagatc       600
cctcttgaca aggagatgca agatgccttt caaaacgcct acatggagct gggaggactc      660
```

-continued

```
ggggagcgag tgctgggctt ctgtcagctg aacctgcctt ctggaaagtt tcctcggggc    720
ttcaaatttg acacggatga gctgaacttt cccacagaga agctctgctt tgtgggcctc    780
atgtctatga ttgatccccc cagagcagct gtgccagatg ctgtgggcaa gtgcagaagt    840
gcaggcatca aggtgatcat ggtgactggg gatcacccta tcacagccaa ggccattgcc    900
aaaggtgtgg gcatcatatc agagggtaac gagactgtgg aagacattgc agccaggctc    960
aacattcctg tgagtcaagt caatcccaga gaagccaagg catgtgtagt gcacggctca    1020
gacctgaagg acatgacttc agagcagctg gatgagatcc tcagggacca cacggagatc    1080
gtgtttgccc ggacctcccc tcagcagaag ctcatcattg tggagggctg tcagaggcag    1140
ggagccatcg tggcagtgac tggtgacggg gtgaacgact cccccgcgct gaagaaggct    1200
gacattggca ttgccatggg catctctggc tctgatgtct ctaagcaggc agctgacatg    1260
atccttctcg acgacaactt tgcctccatt gtgacgggcg tggaggaggg gcgcctgatc    1320
tttgacaacc tgaagaag                                                 1338

<210> SEQ ID NO 9
<211> LENGTH: 1338
<212> TYPE: DNA
<213> ORGANISM: Rattus sp.

<400> SEQUENCE: 9
gtggccaatg tcccagaggg gctgctggct actgtcacgg tgtgtctgac gctgaccgcc    60
aagcgcatgg ctcggaagaa ctgtctggta aagaacctgg aggcggtgga gacgctaggc    120
tccacatcca ccatctgctc cgacaagacc ggcaccctca cccagaaccg catgaccgtc    180
gcccacatgt ggtttgacaa ccagatccac gaggccgaca ctactgagga tcagtcaggg    240
acctctttcg acaagagctc acacacctgg gtggccctgt cccacatcgc cggtctctgc    300
aaccgggctg tcttcaaggg cggcaggat aacatccctg tactcaagag ggacgtggcg    360
ggtgatgcct cagagtccgc cctgcttaag tgcatcgagc tgtcctcggg ttccgtaaag    420
ctgatgcgcg aacgaaacaa gaaagtggcc gagattccct tcaactccac taacaaatac    480
cagctatcca tccatgagac tgaggacccc aatgacaacc gatacctgtt agtgatgaag    540
ggcgcccctg aacgcattct ggaccgctgt gcgaccatcc tctgcagggc aaggagcag    600 cctctggatg aggagatgaa ggaggccttc cagaacgcct acctggagct tggtggcctg    660
ggcgagcgtg tgctgggttt ctgccattac tacctgccgg aggaacagtt ccccaagggc    720
tttgcctttg actgtgatga cgtgaacttc accacagaca acctttgctt cgtgggtctc    780
atgtccatga tcgaccctcc ccgggcagct gtccctgatg ctgtgggcaa atgccgcagt    840
gcaggcatca aggtcatcat ggtcaccggc gatcacccca tcactgcgaa ggccatcgcc    900
aaaggtgtag gcatcatctc cgagggtaac gagactgtgg aggacatcgc tgcccggctc    960
aacatccctg tcagccaggt caaccccagg gatgccaaag cctgtgtgat tcatggcacc    1020
gacctcaagg acttcacctc tgagcagatt gacgagatcc tacagaacca cactgagatc    1080
gtctttgccc gaacctcccc tcagcagaag ctcatcatcg tggagggctg tcagagacag    1140
ggagcaattg tggctgtgac tggcgatggt gtgaatgact cccctgctct gaagaaggct    1200
gatattgggg tggccatggg cattgctggc tctgatgtct ctaagcaggc tgccgacatg    1260
attctgctgg atgacaattt tgcttccatt gtcactggtg tggaggaagg ccgcctgatc    1320
tttgacaacc tgaagaaa                                                 1338
```

<210> SEQ ID NO 10
<211> LENGTH: 1355
<212> TYPE: DNA
<213> ORGANISM: Homo sapiens
<220> FEATURE:
<221> NAME/KEY: UNSURE
<222> LOCATION: (1)..(1355)
<223> OTHER INFORMATION: n = a,c,g,t, any unknown or other

<400> SEQUENCE: 10

| | | | | |
|---|---|---|---|---|
| gtagccaatg | tgccggaagg | tttgctggcc | actgtcacgg | tctgtctgac acttactgcc | 60 |
| aaacgcatgg | caaggaaaaa | ctgcttagtg | aagaacttag | aagctgtgga gaccttgggg | 120 |
| tccacgtcca | ccatctgctc | tgataaaact | ggaactctga | ctcagaaccg atgacagtg | 180 |
| gcccacatgt | ggtttgacaa | tcaaatccat | gaagctgata | cgacagagaa tcagagtggt | 240 |
| gtctcttttg | acaagacttc | agctacctgg | cttgctctgt | ccagaattgc aggtctttgt | 300 |
| aacagggcag | tgtttcaggc | taaccaggaa | aacctaccta | ttcttaagcg ggcagttgca | 360 |
| ggagatgcct | ctgagtcagc | actcttaaag | tgcatagagc | tgtgctgtgg ttccgtgaag | 420 |
| gagatgagag | aaagatacgc | caaaatcgtc | gagatacct | tcaactccac caacaagtac | 480 |
| cagttgtcta | ttcataagaa | ccccaacaca | tcggagcccc | aacacctgtt ggtgatgaag | 540 |
| ggcgccccag | aaaggatcct | agaccgttgc | agctctatcc | tcctcacgg caaggagcag | 600 |
| cccctggatg | aggagctgaa | agacgccttt | cagaacgcct | atttggagct ggggggcctc | 660 |
| ggagaacgag | tcctaggttt | ctgccacctc | tttctgccag | atgaacagtt tcctgaaggg | 720 |
| ttccagtttg | acactgacga | tgtgaatttc | cctatcgata | atctgtgctt tgttgggctc | 780 |
| atctccatga | ttgaccctcc | acgggcggcc | gttcctgatg | ccgtgggcaa atgtcgaagt | 840 |
| gctggaatta | aggtcatcat | ggtcacagga | gaccatccaa | tcacagctaa agctattgcc | 900 |
| aaaggtgtgg | gcatcatctc | agaaggcagt | ggacctatga | gcagaggaaa atcgtggagt | 960 |
| tcacctgcca | cacagccttc | ttcgtcagta | tcgtggtggt | gcagtgggcc gacttggtca | 1020 |
| tctgntaaga | ccaggaggaa | ttcggtcttc | cagcagggga | tgaagaacaa gatcttgata | 1080 |
| tttggcctct | ttgaagagac | agccctggct | gctttccttt | cctactgccc tggaatgggt | 1140 |
| gttgctctta | ggatgtatcc | cctcaaaccn | ntacctggtg | gttctgtgcn cttccctac | 1200 |
| tctcttctca | tcttcgtata | tgacgaagtc | anngaaaact | catcatcagg cgacgccnnn | 1260 |
| ctggcggctg | ggtggannnn | gaaggaaacc | tactattagc | ccccgtcct gcacgccgtg | 1320 |
| gagcatcagg | ccacacactc | tgcatccgac | accca | | 1355 |

<210> SEQ ID NO 11
<211> LENGTH: 1355
<212> TYPE: DNA
<213> ORGANISM: Homo sapiens
<220> FEATURE:
<221> NAME/KEY: UNSURE
<222> LOCATION: (1)..(1355)
<223> OTHER INFORMATION: n = a,c,g,t, any unknown or other

<400> SEQUENCE: 11

| | | | | |
|---|---|---|---|---|
| gtggccaacg | tgcctgaggg | gcttctggcc | actgtcactg | tgtgcctgac cctgacagcc | 60 |
| aagcgcatgg | cacggaagaa | ctgcctggtg | aagaacctgg | aggcggtgga gacgctgggc | 120 |
| tccacgtcca | ccatctgctc | ggacaagacg | ggcaccctca | cccagaaccg catgaccgtc | 180 |
| gcccacatgt | ggttcgacaa | ccaaatccat | gaggctgaca | ccaccgaaga tcagtctggg | 240 |
| gccactttg | acaaacgatc | ccctacgtgg | acggccctgt | ctcgaattgc tggtctctgc | 300 |

-continued

```
aaccgcgccg tcttcaaggc aggacaggag aacatctccg tgtctaagcg ggacacagct      360
ggtgatgcct ctgagtcagc tctgctcaag tgcattgagc tctcctgtgg ctcagtgagg      420
aaaatgagag acagaaaccc caaggtggca gagattcctt tcaactctac caacaagtac      480
cagctgtcta tccacgagcg agaagacagc ccccagagcc nnnacgtgct ggtgatgaag      540
ggggccccag agcgcattct ggaccggtgc tccaccatcc tggtgcaggg caaggagatc      600
ccgctcgaca aggagatgca agatgccttt caaaatgcct acatggagct ggggggactt      660
ggggagcgtg tgctgggatt ctgtcaactg aatctgccat ctggaaagtt tcctcggggc      720
ttcaaattcg acacggatga gctgaacttt cccacggaga agctttgctt tgtggggctc      780
atgtctatga ttgaccctcc ccgggctgct gtgccagatg ctgtgggcaa gtgccgaagc      840
gcaggcatca aggtgatcat ggtaaccggg gatcacccta tcacagccaa ggccattgcc      900
aaaggcgtgg gcatcatatc agagggtaac gagactgtgg aggacattgc agcccggcnt      960
caacattccc atgagtcaan nnngtcanna ccccagagaa gccaaggnca tgcgtggtgc     1020
acggctctga cctgaaggac atganncatc gnnnnngagc agctcgatga gatcctcaag     1080
aaccacacag agatcgtctt tgctcgaacg tctccccagc agaagctcat cattgtggag     1140
ggatgtcaga ggcagggagc cattgtggcc gtgacgggtg acgggtgaa cgactcccct      1200 gcattgaaga aggctgacat tggcattgcc atgggcatct ctggctctga cgtctctaag     1260
caggcagccg acatgatcct gctggatgac aactttgcct ccatcgtcac ggggtggag      1320 gagggccnng cctgatcttt gacaacttga agaaa                                1355
```

<210> SEQ ID NO 12
<211> LENGTH: 1355
<212> TYPE: DNA
<213> ORGANISM: Homo sapiens
<220> FEATURE:
<221> NAME/KEY: UNSURE
<222> LOCATION: (1)..(1355)
<223> OTHER INFORMATION: n = a,c,g,t, any unknown or other

<400> SEQUENCE: 12

```
gtggccaatg tcccagaggg tctgctggcc actgtcactg tgtgtctgac cgtgaccgcc       60
aagcgcatgg cccggaagaa ctgcctggtg aagaacctgg aggctgtaga ccctgggc        120 tccacgtcca ccatctgctc agataagaca gggaccctca ctcagaaccg catgacagtc      180
gcccacatgt ggtttgacaa ccagatccac gaggctgaca ccactgagga ccagtcaggg      240
acctcatttg acaagagttc gcacacctgg gtggccctgt ctcacatcgc tgggctctgc      300
aatcgcgctg tcttcaaggg tggtcaggac aacatccctg tgctcaagag ggatgtggct      360
ggggatgcgt ctgagtctgc cctgctcaag tgcatcgagc tgtcctctgg ctccgtgaag      420
ctgatgcgtg aacgaaacaa gaaagtggct gagattccct tcaattccac caacaaatac      480
cagctctcca tccatgagac cgaggacccc aacgacaacc gatacctgct ggtgatgaag      540
ggtgcccccg agcgcatcct ggaccgctgc tccaccatcc tgctacaggg caaggagcag      600
cctctggacg aggaaatgaa ggaggccttt cagaatgcct accttgagct cggtggcctg      660
ggcgagcgcg tgcttggttt ctgccattat tacctgcccg aggagcagta tcccaaggc      720 tttgccttcg actgtgatga cgtgaacttc accacggaca acctctgctt tgtgccgctc      780
atgtccatga tcggcccacc ccgggcagcc gtccctgacg cggtgggcaa gtgtcgcagc      840
gcaggcatca aggtcatcat ggtcaccggc gatcacccca tcacgccaa ggccattgcc       900 aagggtgtgg gcatcatctc tgagggcaac gagactgtgg aggacatcgc cgcccggcnt      960
```

```
caacattccc gtcagccagn nnngttanna cccccgggat gccaaggncc tgcgtgatcc      1020
acggcaccga cctcaaggac ttcanncctc cnnnnngagc aaatcgacga gatcctgcag      1080
aatcacaccg agatcgtctt cgcccgcaca tcccccccagc agaagctcat cattgtggag     1140
ggctgtcaga gacagggtgc aattgtggct gtgaccgggg atggtgtgaa cgactccccc     1200
gctctgaaga aggccgacat tggggtggcc atgggcatcg ctggctctga cgtctccaag     1260
caggcagctg acatgatcct gctggacgac aactttgcct ccatcgtcac aggggtggag     1320
gagggccnng cctgatcttc gacaacctaa agaag                                1355
```

```
<210> SEQ ID NO 13
<211> LENGTH: 7
<212> TYPE: PRT
<213> ORGANISM: Artificial Sequence
<220> FEATURE:
<223> OTHER INFORMATION: IgE-dependent histamine-releasing factor
      binding peptide

<400> SEQUENCE: 13

Leu Val Thr Tyr Pro Leu Pro
 1               5

<210> SEQ ID NO 14
<211> LENGTH: 7
<212> TYPE: PRT
<213> ORGANISM: Artificial Sequence
<220> FEATURE:
<223> OTHER INFORMATION: IgE-dependent histamine-releasing factor
      binding peptide

<400> SEQUENCE: 14

Trp Tyr Val Tyr Pro Ser Met
 1               5

<210> SEQ ID NO 15
<211> LENGTH: 7
<212> TYPE: PRT
<213> ORGANISM: Artificial Sequence
<220> FEATURE:
<223> OTHER INFORMATION: IgE-dependent histamine-releasing factor
      binding peptide

<400> SEQUENCE: 15

Trp Glu Phe Pro Gly Trp Met
 1               5

<210> SEQ ID NO 16
<211> LENGTH: 7
<212> TYPE: PRT
<213> ORGANISM: Artificial Sequence
<220> FEATURE:
<223> OTHER INFORMATION: IgE-dependent histamine-releasing factor
      binding peptide

<400> SEQUENCE: 16

Ala Tyr Val Tyr Pro Ser Met
 1               5

<210> SEQ ID NO 17
<211> LENGTH: 7
<212> TYPE: PRT
<213> ORGANISM: Artificial Sequence
<220> FEATURE:
<223> OTHER INFORMATION: IgE-dependent histamine-releasing factor
      binding peptide
```

```
<400> SEQUENCE: 17

Trp Ala Val Tyr Pro Ser Met
 1               5

<210> SEQ ID NO 18
<211> LENGTH: 7
<212> TYPE: PRT
<213> ORGANISM: Artificial Sequence
<220> FEATURE:
<223> OTHER INFORMATION: IgE-dependent histamine-releasing factor
      binding peptide

<400> SEQUENCE: 18

Trp Tyr Ala Tyr Pro Ser Met
 1               5

<210> SEQ ID NO 19
<211> LENGTH: 7
<212> TYPE: PRT
<213> ORGANISM: Artificial Sequence
<220> FEATURE:
<223> OTHER INFORMATION: IgE-dependent histamine-releasing factor
      binding peptide

<400> SEQUENCE: 19

Trp Tyr Val Ala Pro Ser Met
 1               5

<210> SEQ ID NO 20
<211> LENGTH: 7
<212> TYPE: PRT
<213> ORGANISM: Artificial Sequence
<220> FEATURE:
<223> OTHER INFORMATION: IgE-dependent histamine-releasing factor
      binding peptide

<400> SEQUENCE: 20

Trp Tyr Val Tyr Lys Ser Met
 1               5

<210> SEQ ID NO 21
<211> LENGTH: 7
<212> TYPE: PRT
<213> ORGANISM: Artificial Sequence
<220> FEATURE:
<223> OTHER INFORMATION: IgE-dependent histamine releasing factor
      binding peptide

<400> SEQUENCE: 21

Trp Tyr Val Tyr Pro Ala Met
 1               5

<210> SEQ ID NO 22
<211> LENGTH: 7
<212> TYPE: PRT
<213> ORGANISM: Artificial Sequence
<220> FEATURE:
<223> OTHER INFORMATION: IgE-dependent histamine releasing factor
      binding peptide

<400> SEQUENCE: 22

Trp Tyr Ala Tyr Pro Ser Ala
 1               5
```